(12) United States Patent
Cocker et al.

(10) Patent No.: US 7,320,682 B2
(45) Date of Patent: *Jan. 22, 2008

(54) SAFETY DEVICE

(75) Inventors: Robin Craig Cocker, Cambridgeshire (GB); Anthony Jonathan Bedford, Cambridgeshire (GB)

(73) Assignee: Tyco Healthcare Group LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/147,063

(22) Filed: May 17, 2002

(65) Prior Publication Data

US 2002/0193748 A1    Dec. 19, 2002

Related U.S. Application Data

(63) Continuation-in-part of application No. PCT/GB00/04416, filed on Nov. 20, 2000.

(30) Foreign Application Priority Data

Nov. 18, 1999 (GB) ................. 9927313.8
Jul. 6, 2000    (GB) ................. 0016676.9

(51) Int. Cl.
    *A61M 5/32*    (2006.01)
(52) U.S. Cl. ............... 604/198; 604/192; 604/263; 604/110
(58) Field of Classification Search ............. 604/192, 604/198, 110, 263, 208–210
    See application file for complete search history.

(56) References Cited

U.S. PATENT DOCUMENTS

| | | | |
|---|---|---|---|
| 1,779,451 A | 10/1930 | Sponsel | |
| 2,559,474 A | 7/1951 | Son | 128/215 |
| 2,700,385 A | 1/1955 | Ortiz | 128/215 |
| 2,836,942 A | 6/1958 | Miskel | 53/25 |
| 2,845,065 A | 7/1958 | Gabriel | |
| 2,854,976 A | 10/1958 | Heydrich | 128/221 |
| 2,925,083 A | 2/1960 | Craig | |
| 2,953,243 A | 9/1960 | Roehr | 206/43 |
| 3,021,942 A | 2/1962 | Hamilton | 206/43 |
| 3,073,307 A | 1/1963 | Stevens | 128/221 |
| 3,074,542 A | 1/1963 | Myerson et al. | 206/43 |
| 3,134,380 A | 5/1964 | Aramao | |
| 3,255,873 A | 6/1966 | Speelman | 206/56 |
| 3,294,231 A | 12/1966 | Vanderbeck | 206/63 |
| 3,323,523 A | 6/1967 | Scislowicz et al. | 128/214 |
| 3,329,149 A | 7/1967 | Waldman, Jr. | 128/221 |
| 3,333,682 A | 8/1967 | Burke | 206/43 |
| 3,367,488 A | 2/1968 | Hamilton | 206/63 |
| 3,485,239 A | 12/1969 | Vanderbeck | 128/218 |
| 3,537,452 A | 11/1970 | Wilks | 128/214 |
| 3,587,575 A | 6/1971 | Lichtenstein | 128/215 |
| 3,610,240 A | 10/1971 | Harautuncian | 128/214 |

(Continued)

FOREIGN PATENT DOCUMENTS

DE    19518803    12/1995

(Continued)

*Primary Examiner*—Kevin C. Sirmons
*Assistant Examiner*—Laura C. Schell

(57) ABSTRACT

A safety device for a needle is provided. The device includes a spring biased sheath which acts to cover the needle before and after use. The safety device also includes a spring biased lock which is operable to lock the sheath in a safe position unless the biasing force of the lock is countered by a user.

14 Claims, 15 Drawing Sheets

U.S. PATENT DOCUMENTS

| | | | |
|---|---|---|---|
| 3,645,835 A | 2/1972 | Hodgson | 161/146 |
| 3,658,061 A | 4/1972 | Hall | 128/214 |
| 3,828,775 A | 8/1974 | Armel | 128/218 |
| 3,840,008 A | 10/1974 | Noiles | 128/221 |
| 3,890,971 A | 6/1975 | Leeson et al. | 128/218 |
| 3,904,033 A | 9/1975 | Haerr | 206/349 |
| 3,918,446 A | 11/1975 | Buttaravoli | 128/133 |
| 3,934,722 A | 1/1976 | Goldberg | 206/365 |
| 3,968,876 A | 7/1976 | Sievenpiper | 206/365 |
| 4,040,419 A | 8/1977 | Goldman | 128/215 |
| 4,106,621 A | 8/1978 | Sorenson | 206/365 |
| 4,113,090 A | 9/1978 | Carstens | 206/365 |
| 4,139,009 A | 2/1979 | Alvarez | 128/218 |
| 4,175,008 A | 11/1979 | White | 435/295 |
| 4,270,536 A | 6/1981 | Lemelson | 128/218 |
| 4,300,678 A | 11/1981 | Gyure et al. | 206/364 |
| 4,375,849 A | 3/1983 | Hanifl | 206/366 |
| 4,430,082 A | 2/1984 | Schwabacher | 604/263 |
| 4,592,744 A | 6/1986 | Jagger et al. | 604/192 |
| 4,634,428 A | 1/1987 | Cuu | 604/110 |
| 4,643,722 A | 2/1987 | Smith, Jr. | 604/192 |
| 4,659,330 A | 4/1987 | Nelson et al. | 604/192 |
| 4,664,259 A | 5/1987 | Landis | 206/365 |
| 4,664,654 A | 5/1987 | Strauss | 604/198 |
| 4,681,567 A | 7/1987 | Masters et al. | 604/198 |
| 4,695,274 A | 9/1987 | Fox | 604/198 |
| 4,702,738 A | 10/1987 | Spencer | 604/198 |
| 4,723,943 A | 2/1988 | Spencer | 604/198 |
| 4,725,267 A | 2/1988 | Vaillancourt | |
| 4,728,320 A | 3/1988 | Chen | 604/110 |
| 4,728,321 A | 3/1988 | Chen | 604/110 |
| 4,731,059 A | 3/1988 | Wanderer et al. | 604/192 |
| 4,735,311 A | 4/1988 | Lowe et al. | 206/365 |
| 4,735,618 A * | 4/1988 | Hagen | 604/192 |
| 4,737,144 A | 4/1988 | Choksi | 604/198 |
| 4,738,663 A | 4/1988 | Bogan | 604/198 |
| 4,743,233 A | 5/1988 | Schneider | 604/192 |
| 4,747,836 A | 5/1988 | Luther | 604/198 |
| 4,747,837 A | 5/1988 | Hauck | 604/198 |
| 4,772,272 A | 9/1988 | McFarland | 604/198 |
| 4,778,453 A | 10/1988 | Lopez | 604/110 |
| 4,781,697 A | 11/1988 | Slaughter | 604/192 |
| 4,782,841 A | 11/1988 | Lopez | 128/164 |
| 4,790,828 A * | 12/1988 | Dombrowski et al. | 604/198 |
| 4,795,432 A | 1/1989 | Karczmer | 604/110 |
| 4,795,443 A | 1/1989 | Permenter et al. | 604/198 |
| 4,801,295 A | 1/1989 | Spencer | 604/198 |
| 4,804,372 A | 2/1989 | Laico et al. | 604/198 |
| 4,813,426 A | 3/1989 | Haber et al. | 128/763 |
| 4,816,022 A | 3/1989 | Poncy | 604/198 |
| 4,816,024 A | 3/1989 | Sitar et al. | 604/192 |
| 4,819,659 A | 4/1989 | Sitar | 128/764 |
| 4,820,277 A | 4/1989 | Norelli | 604/192 |
| 4,826,490 A | 5/1989 | Byrne et al. | 604/198 |
| 4,826,491 A | 5/1989 | Schramm | 604/198 |
| 4,838,871 A | 6/1989 | Luther | 604/192 |
| 4,840,619 A | 6/1989 | Hughes | 604/187 |
| 4,842,587 A | 6/1989 | Poncy | 604/198 |
| 4,846,796 A | 7/1989 | Carrell et al. | 604/110 |
| 4,846,811 A | 7/1989 | Vanderhoof | 604/263 |
| 4,850,968 A | 7/1989 | Romano | 604/110 |
| 4,850,976 A | 7/1989 | Heinrich et al. | 604/192 |
| 4,850,977 A | 7/1989 | Bayless | |
| 4,850,978 A | 7/1989 | Dudar et al. | 604/201 |
| 4,850,994 A | 7/1989 | Zerbst et al. | 604/198 |
| 4,850,996 A | 7/1989 | Cree | 604/198 |
| 4,858,607 A | 8/1989 | Jordan et al. | 128/314 |
| 4,863,434 A | 9/1989 | Bayless | |
| 4,863,435 A | 9/1989 | Sturman et al. | |
| 4,863,436 A | 9/1989 | Glick | 604/198 |
| 4,867,172 A | 9/1989 | Haber et al. | 128/763 |
| 4,867,746 A | 9/1989 | Dufresne | 604/192 |
| 4,872,552 A | 10/1989 | Unger | 206/365 |
| 4,874,382 A | 10/1989 | Lindemann et al. | 604/195 |
| 4,874,383 A | 10/1989 | McNaughton | 604/198 |
| 4,874,384 A | 10/1989 | Nunez | 604/198 |
| 4,883,469 A | 11/1989 | Glazier | 604/192 |
| 4,886,503 A | 12/1989 | Miller | 604/192 |
| 4,887,998 A | 12/1989 | Martin et al. | 604/110 |
| 4,888,001 A | 12/1989 | Schoenberg | 604/162 |
| 4,892,107 A | 1/1990 | Haber | 128/763 |
| 4,892,521 A | 1/1990 | Laico et al. | |
| 4,898,589 A | 2/1990 | Dolgin et al. | 604/198 |
| 4,900,309 A | 2/1990 | Netherton et al. | 604/192 |
| 4,904,244 A | 2/1990 | Harsh et al. | 604/187 |
| 4,911,694 A | 3/1990 | Dolan | 604/198 |
| 4,911,706 A | 3/1990 | Levitt | 604/198 |
| 4,921,490 A | 5/1990 | Spier et al. | |
| 4,927,018 A | 5/1990 | Yang et al. | 206/365 |
| 4,929,241 A | 5/1990 | Kulli | 604/263 |
| 4,935,012 A | 6/1990 | Magre et al. | 604/192 |
| 4,935,013 A | 6/1990 | Haber et al. | |
| 4,936,830 A | 6/1990 | Verlier | 604/110 |
| 4,944,397 A | 7/1990 | Miller | 206/365 |
| 4,944,731 A | 7/1990 | Cole | 604/192 |
| 4,950,249 A | 8/1990 | Jagger et al. | 604/192 |
| 4,950,250 A | 8/1990 | Haber et al. | |
| 4,978,344 A | 12/1990 | Dombrowski et al. | 604/198 |
| 4,982,842 A | 1/1991 | Hollister | 206/365 |
| 4,985,021 A | 1/1991 | Straw et al. | 604/198 |
| 4,994,041 A | 2/1991 | Dombrowski et al. | 604/164 |
| 4,998,922 A * | 3/1991 | Kuracina et al. | 604/192 |
| 5,000,744 A | 3/1991 | Hoffman et al. | 604/232 |
| 5,015,240 A | 5/1991 | Soproni et al. | 604/192 |
| 5,015,242 A | 5/1991 | Heifetz | |
| 5,057,089 A | 10/1991 | Greco | 604/198 |
| 5,059,180 A | 10/1991 | McLees | 604/110 |
| 5,059,184 A | 10/1991 | Dyke | |
| 5,069,669 A | 12/1991 | Kole | |
| 5,078,697 A * | 1/1992 | Rammler | 604/198 |
| 5,092,851 A | 3/1992 | Ragner | |
| 5,108,379 A | 4/1992 | Dolgin et al. | 604/198 |
| RE34,045 E | 8/1992 | McFarland | 604/198 |
| 5,135,509 A | 8/1992 | Olliffe | 604/192 |
| 5,139,489 A | 8/1992 | Hollister | 604/192 |
| 5,147,303 A | 9/1992 | Martin | 604/110 |
| 5,154,285 A | 10/1992 | Hollister | 206/365 |
| 5,176,655 A | 1/1993 | McCormick et al. | 604/198 |
| 5,176,656 A | 1/1993 | Bayless | 604/198 |
| 5,193,552 A | 3/1993 | Columbus et al. | 128/760 |
| 5,195,983 A | 3/1993 | Boese | 604/192 |
| 5,209,739 A | 5/1993 | Talalay | 604/195 |
| 5,232,454 A | 8/1993 | Hollister | 604/192 |
| 5,232,455 A | 8/1993 | Hollister | 604/192 |
| 5,242,417 A | 9/1993 | Paudler | 604/192 |
| 5,242,418 A | 9/1993 | Weinstein | 604/192 |
| 5,246,427 A | 9/1993 | Sturman et al. | 604/192 |
| 5,246,428 A | 9/1993 | Falknor | 604/198 |
| 5,250,031 A | 10/1993 | Kaplan et al. | 604/110 |
| 5,254,099 A | 10/1993 | Kuracina et al. | 604/198 |
| 5,256,152 A | 10/1993 | Marks | |
| 5,256,153 A | 10/1993 | Hake | 604/198 |
| 5,277,311 A | 1/1994 | Hollister | 206/365 |
| 5,290,255 A | 3/1994 | Vallelunga et al. | 604/197 |
| 5,295,963 A | 3/1994 | Deeks | |
| 5,295,972 A | 3/1994 | Mischenko | |
| 5,304,137 A | 4/1994 | Fluke | |
| 5,312,368 A | 5/1994 | Haynes | 604/192 |
| 5,312,369 A | 5/1994 | Arcusin et al. | 604/192 |
| 5,334,158 A | 8/1994 | McLees | 604/110 |
| 5,348,544 A | 9/1994 | Sweeney et al. | 604/192 |
| 5,356,387 A | 10/1994 | Sirbola | |
| 5,356,392 A | 10/1994 | Firth et al. | 604/198 |
| 5,372,589 A | 12/1994 | Davis | 604/180 |

| | | |
|---|---|---|
| 5,374,255 A | 12/1994 | Nathan et al. |
| 5,403,283 A | 4/1995 | Luther .................... 604/164 |
| 5,403,286 A | 4/1995 | Lockwood, Jr. ........... 604/110 |
| 5,407,436 A | 4/1995 | Toft et al. .................. 604/195 |
| 5,411,492 A | 5/1995 | Sturman et al. ........... 604/263 |
| 5,423,765 A | 6/1995 | Hollister ................... 604/192 |
| 5,423,766 A | 6/1995 | Di Cesare ................. 604/192 |
| 5,425,720 A | 6/1995 | Rogalsky et al. .......... 604/198 |
| 5,445,618 A | 8/1995 | Adobbati ................... 604/192 |
| 5,447,501 A | 9/1995 | Karlsson et al. ........... 604/198 |
| 5,466,223 A | 11/1995 | Bressler et al. |
| 5,480,385 A | 1/1996 | Thorne et al. ............. 604/110 |
| 5,486,164 A | 1/1996 | Streck |
| 5,487,733 A | 1/1996 | Caizza et al. .............. 604/110 |
| 5,487,734 A | 1/1996 | Thorne et al. ............. 604/195 |
| 5,490,841 A | 2/1996 | Landis ...................... 604/110 |
| 5,498,243 A | 3/1996 | Vallelunga et al. ........ 604/197 |
| 5,531,694 A | 7/1996 | Clemens et al. ........... 604/110 |
| 5,533,980 A | 7/1996 | Sweeney et al. ........... 604/192 |
| 5,536,240 A | 7/1996 | Edwards et al. ............. 604/22 |
| 5,538,508 A | 7/1996 | Steyn ........................ 604/192 |
| 5,542,927 A | 8/1996 | Thorne et al. ............. 604/110 |
| 5,549,568 A | 8/1996 | Shields ...................... 604/192 |
| 5,549,570 A | 8/1996 | Rogalsky ................... 604/198 |
| 5,549,708 A | 8/1996 | Thorne et al. ............. 604/110 |
| 5,562,629 A | 10/1996 | Haughton et al. .......... 604/158 |
| 5,562,631 A | 10/1996 | Bogert ....................... 604/164 |
| 5,573,510 A | 11/1996 | Isaacson ................... 604/158 |
| 5,584,816 A | 12/1996 | Gyure et al. ............... 604/192 |
| 5,584,818 A | 12/1996 | Morrison ................... 604/110 |
| 5,599,318 A | 2/1997 | Sweeney et al. ........... 604/263 |
| 5,611,782 A | 3/1997 | Haedt ........................ 604/198 |
| 5,643,220 A | 7/1997 | Cosme ...................... 604/192 |
| 5,672,161 A | 9/1997 | Allen et al. ................ 604/263 |
| 5,695,474 A | 12/1997 | Daugherty ................. 604/162 |
| 5,695,477 A | 12/1997 | Sfikas ........................ 604/241 |
| 5,700,249 A | 12/1997 | Jenkins ...................... 604/263 |
| 5,735,827 A | 4/1998 | Adwers et al. ............. 604/263 |
| 5,738,665 A | 4/1998 | Caizza et al. .............. 604/263 |
| 5,746,718 A | 5/1998 | Steyn ........................ 604/192 |
| 5,746,726 A | 5/1998 | Sweeney et al. ........... 604/263 |
| 5,755,699 A | 5/1998 | Blecher et al. ............. 604/198 |
| 5,814,018 A | 9/1998 | Elson et al. ................ 604/110 |
| 5,817,064 A | 10/1998 | DeMarco et al. ........... 604/263 |
| 5,823,997 A | 10/1998 | Thorne ...................... 604/110 |
| 5,843,041 A | 12/1998 | Hake et al. ................ 604/198 |
| 5,879,330 A | 3/1999 | Bell ............................. 604/93 |
| 5,891,092 A | 4/1999 | Castellano |
| 5,910,130 A | 6/1999 | Caizza et al. .............. 604/110 |
| 5,910,132 A | 6/1999 | Schultz |
| 5,919,168 A | 7/1999 | Wheeler .................... 604/198 |
| 5,921,969 A | 7/1999 | Vallelunga et al. ........ 604/263 |
| 5,925,020 A | 7/1999 | Nestell ...................... 604/198 |
| 5,951,522 A | 9/1999 | Rosato et al. .............. 604/177 |
| 5,951,525 A | 9/1999 | Thorne et al. ............. 604/198 |
| 5,957,892 A | 9/1999 | Thorne ...................... 604/162 |
| 5,976,111 A | 11/1999 | Hart |
| 5,980,488 A | 11/1999 | Thorne ...................... 604/110 |
| 5,997,504 A | 12/1999 | Bell ............................. 604/93 |
| 6,015,397 A | 1/2000 | Elson et al. ................ 604/192 |
| 6,036,675 A | 3/2000 | Thorne et al. ............. 604/232 |
| 6,149,629 A | 11/2000 | Wilson et al. ............. 604/198 |
| 6,171,284 B1 | 1/2001 | Kao et al. .................. 604/192 |
| RE37,110 E | 3/2001 | Hollister ................... 206/365 |
| 6,224,576 B1 | 5/2001 | Thorne et al. ............. 604/198 |
| RE37,252 E | 7/2001 | Hollister ................... 206/364 |
| 6,254,575 B1 | 7/2001 | Thorne, Jr. et al. ........ 604/198 |
| 6,280,420 B1 | 8/2001 | Ferguson et al. ........... 604/198 |
| 6,334,857 B1 | 1/2002 | Hollister et al. ........... 604/263 |
| 6,582,397 B2 | 6/2003 | Alesi et al. ................. 604/110 |
| 6,592,556 B1 | 7/2003 | Thorne ...................... 604/192 |
| 6,635,032 B2 | 10/2003 | Ward, Jr. .................... 604/192 |
| 6,719,731 B2 | 4/2004 | Parmigiani |
| 6,986,759 B1 * | 1/2006 | Jeremijevic ................ 604/198 |
| 2001/0039401 A1 | 11/2001 | Ferguson et al. |
| 2002/0004650 A1 | 1/2002 | Kuracina et al. |
| 2002/0072716 A1 | 6/2002 | Barrus et al. |
| 2003/0004465 A1 | 1/2003 | Ferguson et al. |
| 2003/0181870 A1 | 9/2003 | Bressler et al. |
| 2003/0181871 A1 | 9/2003 | Wilkinson et al. |

FOREIGN PATENT DOCUMENTS

| | | |
|---|---|---|
| EP | 0 144 483 | 6/1985 |
| EP | 0 344 606 A2 | 12/1989 |
| EP | 0 457 477 B1 | 11/1991 |
| EP | 0 485 345 B1 | 5/1992 |
| EP | 0 533 308 A1 | 3/1993 |
| EP | 0 585 391 B1 | 3/1994 |
| EP | 0 597 857 B1 | 5/1994 |
| EP | 0 603 365 B1 | 6/1994 |
| EP | 0 626 924 B1 | 12/1994 |
| EP | 0 654 281 B1 | 5/1995 |
| EP | 0 705 613 B1 | 4/1996 |
| EP | 0 713 710 A1 | 5/1996 |
| EP | 0 807 443 A2 | 11/1997 |
| EP | 0 815 888 A2 | 1/1998 |
| EP | 0 815 890 A2 | 1/1998 |
| EP | 0 819 441 A1 | 1/1998 |
| EP | 0 832 659 A2 | 4/1998 |
| EP | 0 832 660 A2 | 4/1998 |
| EP | 1 092 443 A2 | 4/2001 |
| EP | 1 116 493 A1 | 7/2001 |
| GB | 1233302 | 5/1971 |
| GB | 2 283 429 A | 5/1995 |
| GB | 2 369 779 | 12/2002 |
| JP | 10-76007 | 3/1998 |
| JP | 10-127765 | 5/1998 |
| NL | 9000909 | 4/1990 |
| NL | 9001664 | 7/1990 |
| WO | WO 87/07162 | 12/1987 |
| WO | WO 89/04681 | 6/1989 |
| WO | WO 89/07955 | 9/1989 |
| WO | WO 93/17732 | 9/1993 |
| WO | WO 94/19036 | 9/1994 |
| WO | WO 97/31666 | 4/1997 |
| WO | WO 98/07463 | 2/1998 |
| WO | WO 98/10816 | 3/1998 |
| WO | WO 98/11928 | 3/1998 |
| WO | WO 98/13081 | 4/1998 |
| WO | WO 00/16832 | 3/2000 |
| WO | WO 00/38765 | 6/2000 |
| WO | WO 01/32244 A1 | 5/2001 |
| WO | WO 01/33241 A1 | 5/2001 |

* cited by examiner

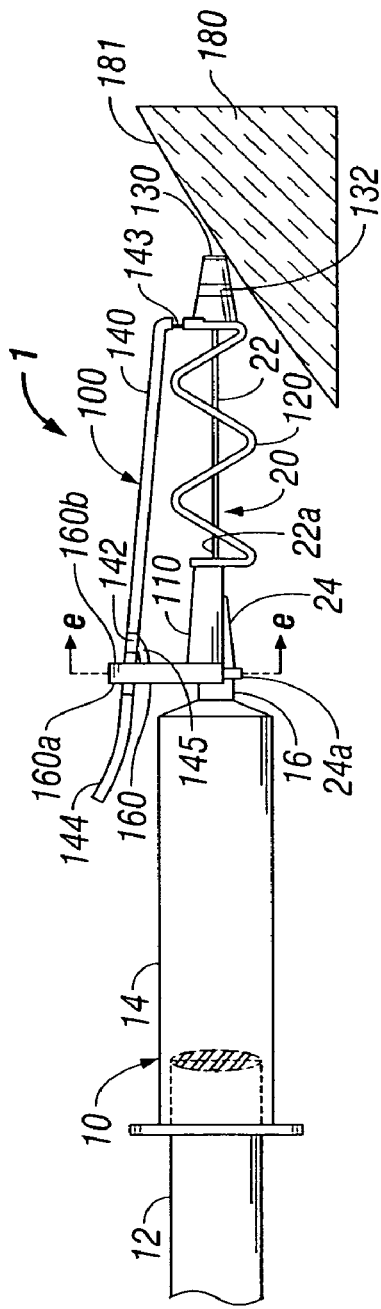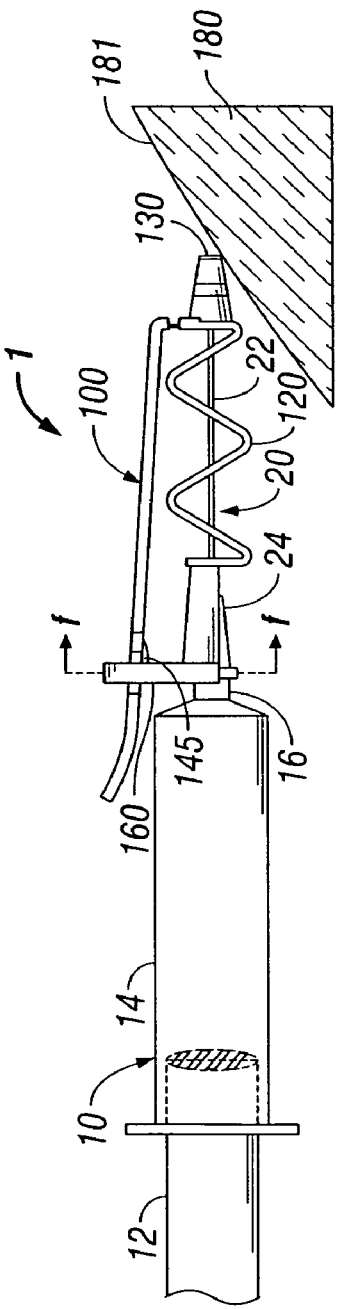
FIG. 1a
FIG. 1b

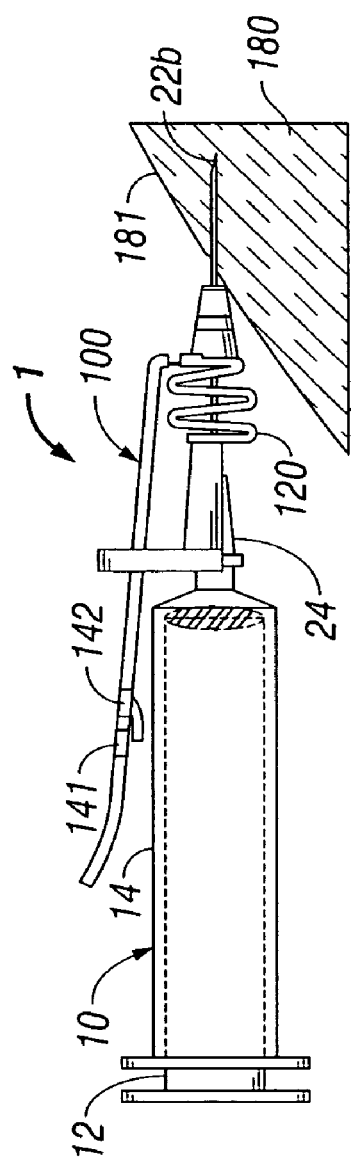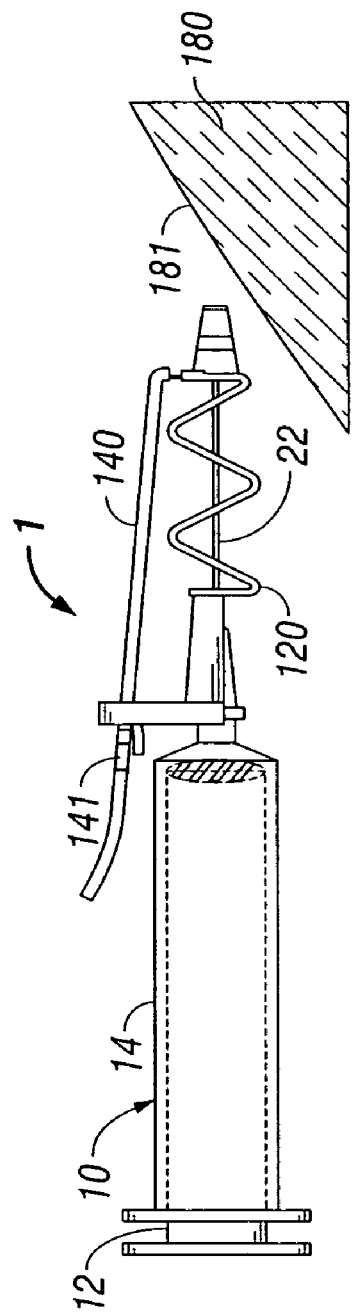
FIG. 1c
FIG. 1d

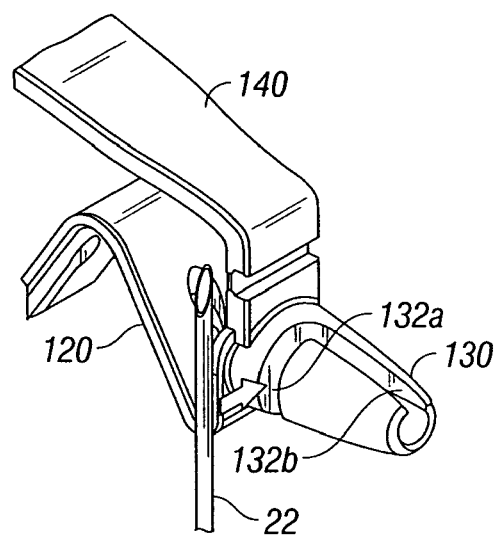
FIG. 1l
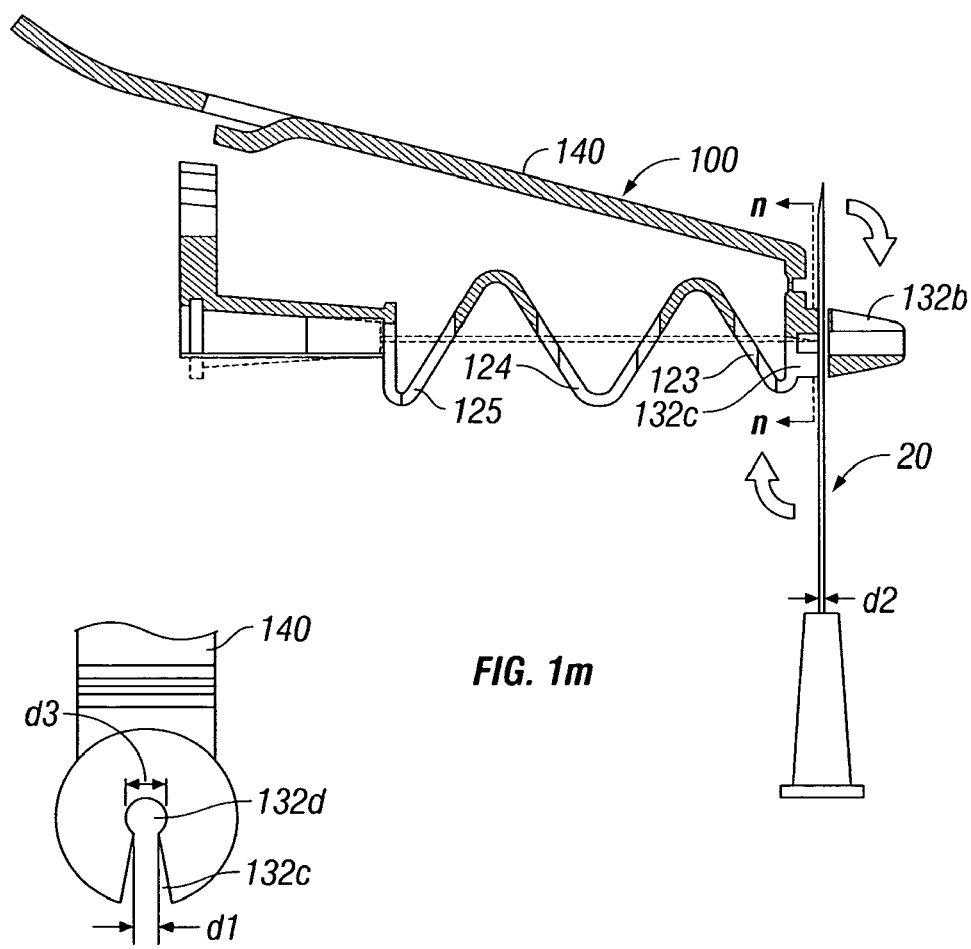
FIG. 1m
FIG. 1n

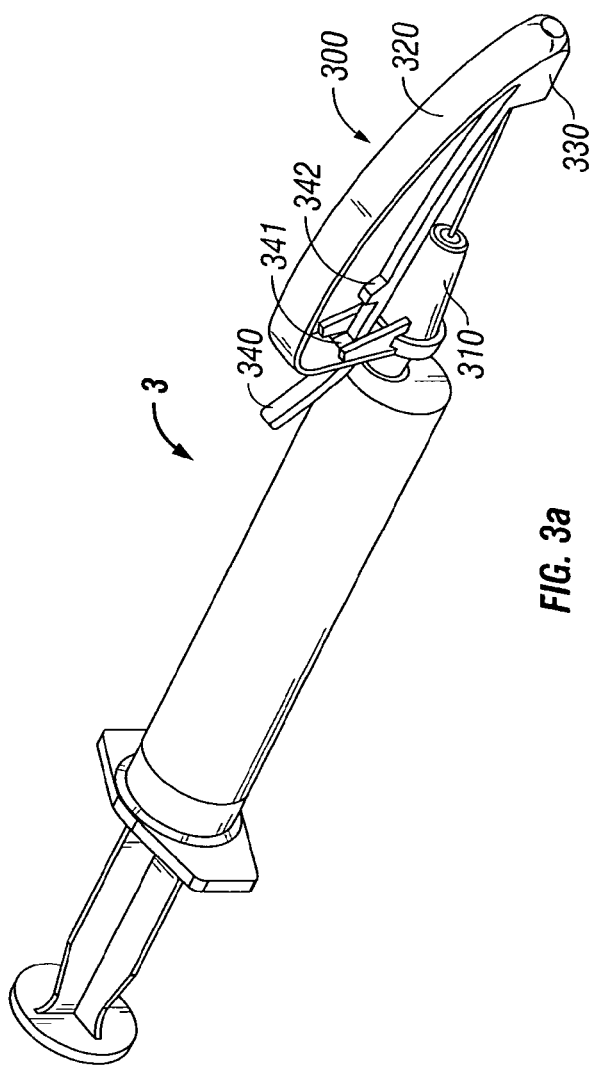
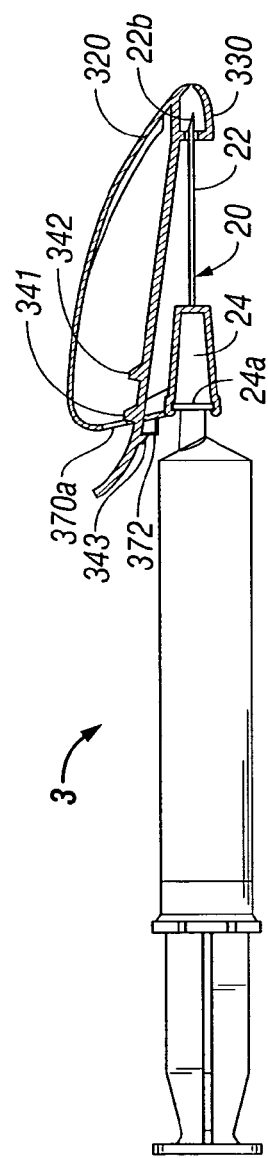
FIG. 3a
FIG. 3b

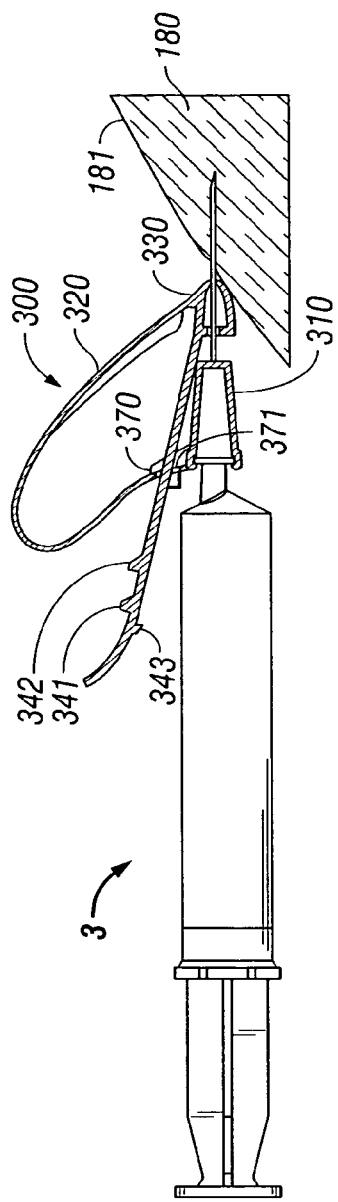
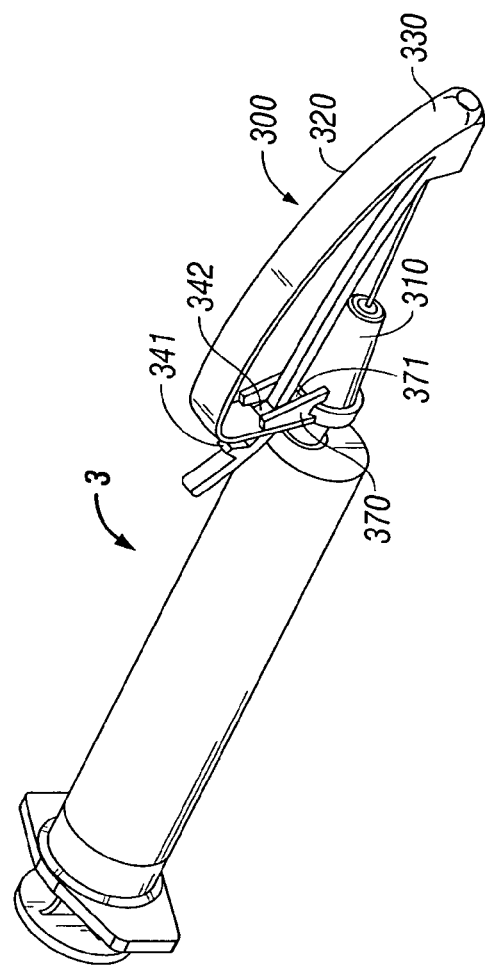
FIG. 3c
FIG. 3d

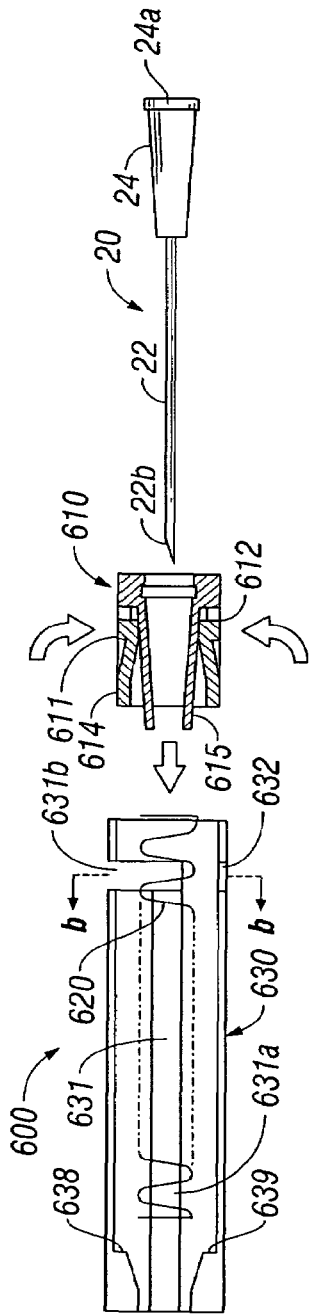
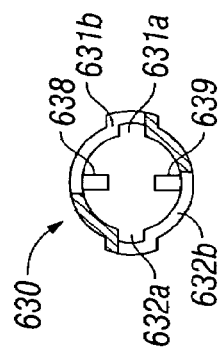
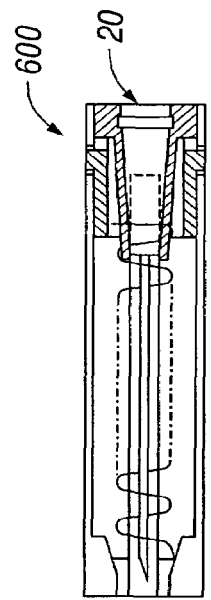
FIG. 6a
FIG. 6b
FIG. 6c

SAFETY DEVICE

This application is a Continuation-in-Part of International Patent Application No. PCT/GB00/04416, filed Nov. 20, 2000, which claims priority of Great Britain Application No. 9927313.8 filed Nov. 18, 1999, and Great Britain Application No. 0016676.9, filed Jul. 6, 2000.

The present invention relates to a safety device, and a method of manufacture thereof, for hypodermic needles.

There is a known problem associated with hypodermic needles, which is that once a hypodermic needle has been used on a patient, it may be contaminated with an infection from the patient, and there is therefore a risk that the needle may pass on the infection if it is allowed to come into contact with another person. Similarly, if a needle accidentally pricks one person before it is used on a patient, an infection may be passed onto the patient from the person accidentally pricked. Undesirable pricking of this nature will hereinafter be referred to as "needle stick".

A number of safety devices have been proposed in an attempt to counter the above described problems. Some such devices are combined needle and syringe arrangements in which the needle may be retracted into the body of the syringe by applying additional pressure on the syringe plunger once it has been pushed to the end of the syringe cylinder (i.e. once all of the fluid to be injected has been ejected from the syringe). While the syringe and needle arrangement is transported and stored, a plastic cap is fitted over the needle. There are a number of problems with a device of this type. Firstly, this device is only suitable for injecting fluid into a patient and not for taking a sample from a patient because the retraction of the needle is activated once the plunger is fully pushed into the cylinder and not when it is partially withdrawn from the cylinder as would be the case after the taking of a sample. Also, the person who is to give the injection must remove the plastic cap some time before the injection takes place, and from this moment on until the needle is retracted, the device is unsafe. Once the injection is completed, the operator of the needle must remember to perform the action to cause the needle to retract. To maximise safety, this should be performed whilst the needle is still within the patient. However, this is painful for the patient. Also, the operator may simply omit to retract the needle for whatever reason, thus leaving the needle exposed and unsafe.

To counter this last problem, it has been proposed to include a time fuse mechanism which is activated upon, for example, hydration (e.g. by receiving a blood sample or a liquid to be injected into the syringe). However, the needle will be unsafe for the duration of the time fuse period and can cause problems if, for example, the retraction is automatically activated during an injection.

U.S. Pat. No. 5,976,111 describes an alternative safety device for a hypodermic needle. The described device includes a stem portion through which fluid may flow between the syringe mounted on a proximal end of the stem and a needle mounted on a distal end of the stem. Telescopically mounted around the stem is a sheath cylinder. The sheath cylinder may slide over the stem from a first, exposed, position in which the point of the needle is exposed, to a second position in which the whole of the needle is covered by the sheath. A helical metal spring urges the sheath into the second position. A pair of leaf spring arms which are biased radially outwardly are mounted onto the stem and lock the sheath in the second position (the needle is therefore safe while the sheath is locked in the second position). A ring is also slidably mounted on the stem and may be used to unlock the sheath by forcing the leaf spring arms flat into the stem portion to permit an injection to take place. During an injection the skin of the patient pushes the sheath cylinder (and also the unlocking ring) back into the first position, exposing the needle point which may therefore pierce the patient's skin. Upon completion of the injection, the sheath is urged back (due to the spring) into the second position as the needle is withdrawn from the patient, thus re-covering the needle. While the sheath is pushed back over the stem portion towards the first position, the unlocking ring is also pushed back into a position where it no longer restrains the leaf spring arms; therefore, when the sheath cylinder returns back to the second "safe" position the leaf spring arms are released and they spring out into locking engagement with the sheath to prevent the sheath from sliding back into the first, exposed, position again.

The device described in U.S. Pat. No. 5,976,111 satisfies many of the safety requirements associated with hypodermic needles discussed above. However, it nonetheless suffers from a number of problems, which it would be desirable to overcome. Importantly, from a safety perspective, the safety device may be left in an unsafe primed position by sliding the unlocking ring to cover the leaf spring arms and leaving it in that position. Therefore, if the assembly were left in such an unsafe position, a needle stick accident could occur by pressing the primed device accidentally against someone's skin. Furthermore, all of the described embodiments of the device require at least five separate components to be manufactured and then assembled. This renders the cost of the device significantly more than a conventional needle and needle-luer combination (a needle-luer is a small member which is adapted to fit onto a syringe and into which the base of the needle is mounted). Also, because the needle is mounted directly to the stem of the described safety device, a needle manufacturer would have to significantly alter its conventional manufacturing process for producing needle and needle-luer combinations to manufacture the described device.

The present invention seeks to provide an alternative safety device for a hypodermic needle.

According to a first aspect of the present invention, there is provided a safety device for a hypodermic needle comprising needle receiving means, a sheath portion for surrounding and protecting the needle point when in a safe position, the sheath portion being translatable along the direction of the needle away from the needle point into an injection position in which the needle point projects beyond the sheath portion; a resilient portion for biasing the sheath portion into the safe position; and a biased locking portion which automatically locks the sheath portion in a safe position unless actuated by a user against the locking bias.

In the preferred embodiments described below, the needle point is not exposed to the atmosphere unless it is actively misused by a user. It is intended in all of the described embodiments that the sheath portion slides back along the needle only as a result of being pressed against an injection surface. In such a case, the needle point passes directly from the sheath portion into the object being injected without substantial exposure to the atmosphere. It is possible for a user to pull the sheath to expose the needle without pressing the sheath against an injection surface, and this may be useful for certain difficult injections, however, such exposure of the needle requires the active participation of the user. If the safety device is released in such a position (e.g. because it is dropped), the safety device will return automatically into a safe locked position.

The design of the preferred embodiments to be discussed below allows the safety device to be manufactured using a one step injection moulding process. This therefore reduces the manufacturing and assembly costs and hence the overall costs of the needle assembly. For such embodiments, the safety device can be made from polypropylene, polyethylene, acetal or the like.

In some embodiments, in order to assist in the assembly of the safety device and the needle, the safety device includes a twisted slot arrangement whereby a conventionally manufactured needle may be inserted into the safety device with little risk of the point of the needle being damaged by contacting a surface of the safety device. The safety device may receive the needle on its own or when already mounted on a needle-luer, in which case the safety device includes a needle-luer fitting portion. This permits needle manufacturers to make a sub-assembly of a safety device and a needle and needle-luer combination without significantly altering their process for manufacturing needle and needle-luer combinations simply by having a separate process for manufacturing the safety devices and then assembling the needle and needle-luer combinations into the safety devices.

The resilient portion may be provided solely from the plastics material from which the rest of the safety device is manufactured. This has the advantage of lower manufacturing costs and easier assembly. Alternatively, a metallic member (such as a coil spring) could be used to provide some or all of the required resilience. In some such embodiments, the metallic member may be incorporated into the device by means of an insert or outsert moulding method which eases manufacture of the safety device.

Where the resilient portion is provided solely from the plastics material, the safety device preferably includes a mechanism for coping with "plastic creep". This ensures that the device may be stored in a safe storage position for a relatively long period of time without the risk of the device failing to automatically return into a locked, safe position after use because of plastic creep.

In order that the present invention may be better understood, preferred embodiments thereof will now be described, by way of example only, with reference to the accompanying drawings in which:

FIG. 1a is a cross sectional view along the length of a hypodermic syringe, needle and safety device assembly according to a first embodiment of the present invention in a storage position;

FIG. 1b is a cross-sectional view along the length of the assembly of FIG. 1a in a primed position;

FIG. 1c is a cross-sectional view along the length of the assembly of FIG. 1b in use whilst an injection is being given;

FIG. 1d is a cross-sectional view along the length of the assembly of FIG. 1a in the position which it adopts after completion of an injection;

FIG. 1l is a perspective view of the tip of the safety device of FIG. 1a in the position in which it is moulded, together with a needle and needle-luer combination, illustrating how the combination is mounted in the safety device;

FIG. 1m is a cross-sectional view of the safety device shown in FIG. 1a in the position in which it is moulded, together with a needle and needle-luer combination, illustrating how the combination is mounted in the safety device;

FIG. 1n is a cross-sectional view through the safety device shown in FIG. 1a along the line n-n of FIG. 1m;

FIG. 3a is a perspective view of a syringe, needle and safety device assembly according to a third embodiment which incorporates a single turn leaf spring as a resilient member;

FIG. 3b is a cross-sectional view of the syringe assembly shown in FIG. 3a;

Figure 4A:
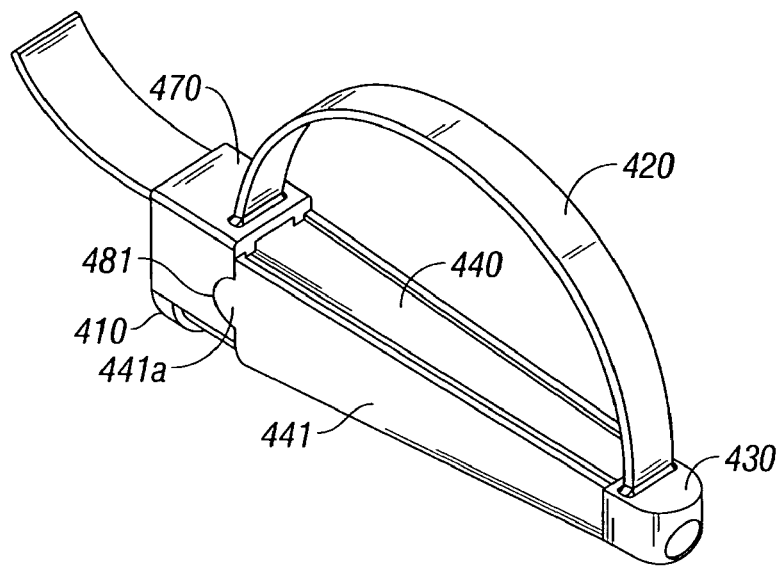
Figure 4B:
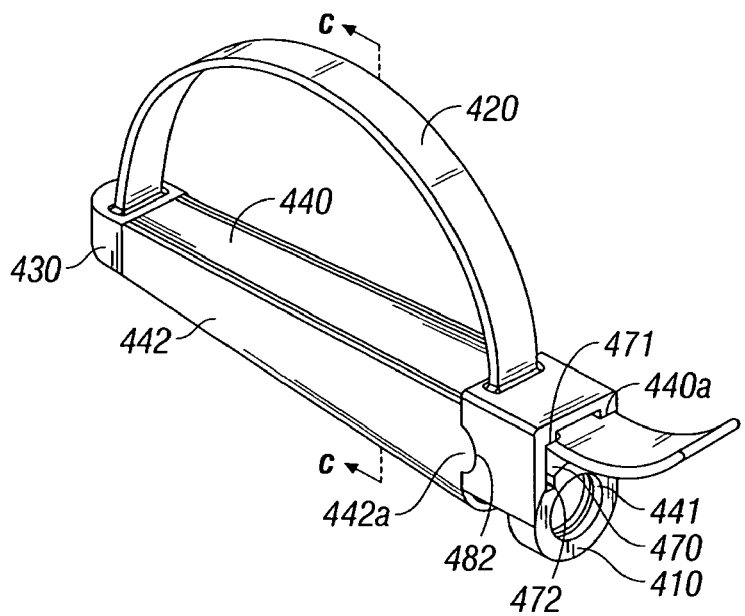
Figure 4C:
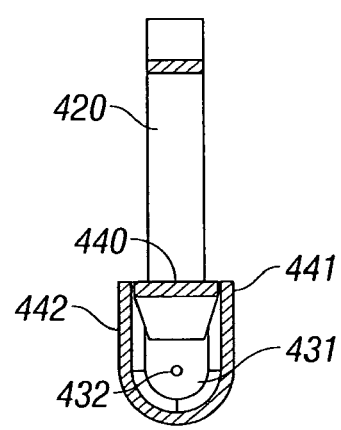
Figure 5A:
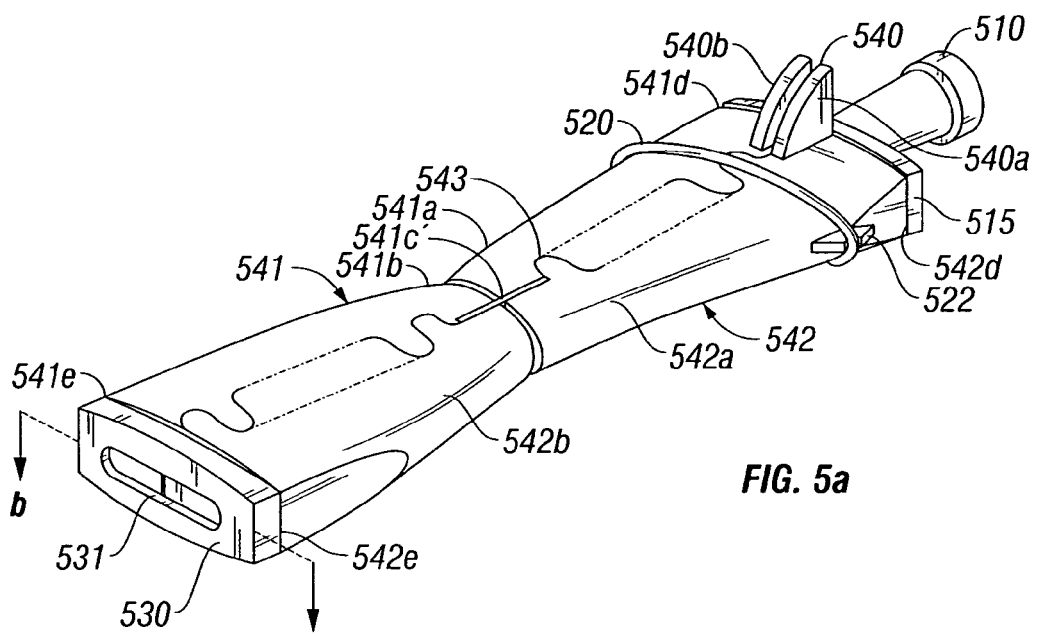
Figure 5B:
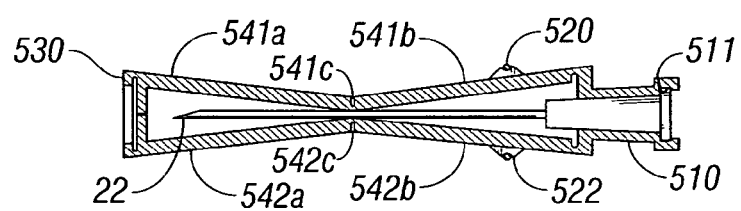
Figure 5C:
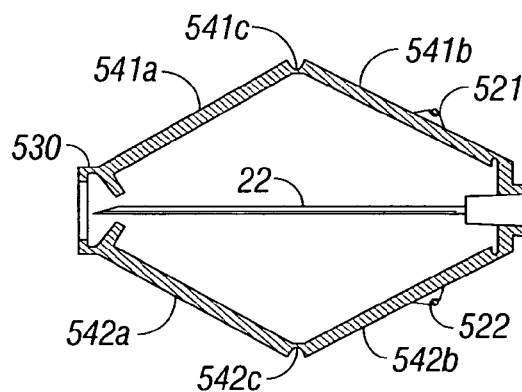
Figure 5D:
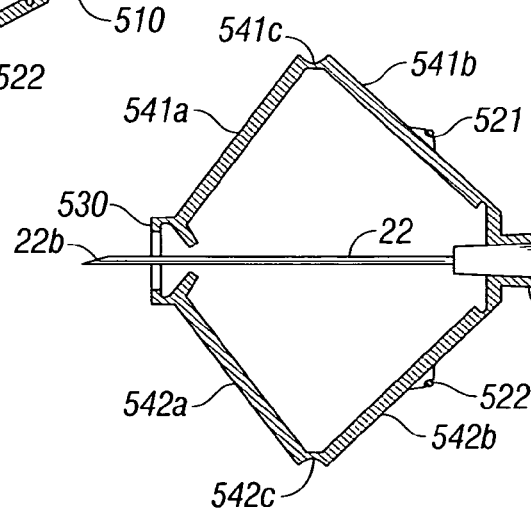
Figure 5E:
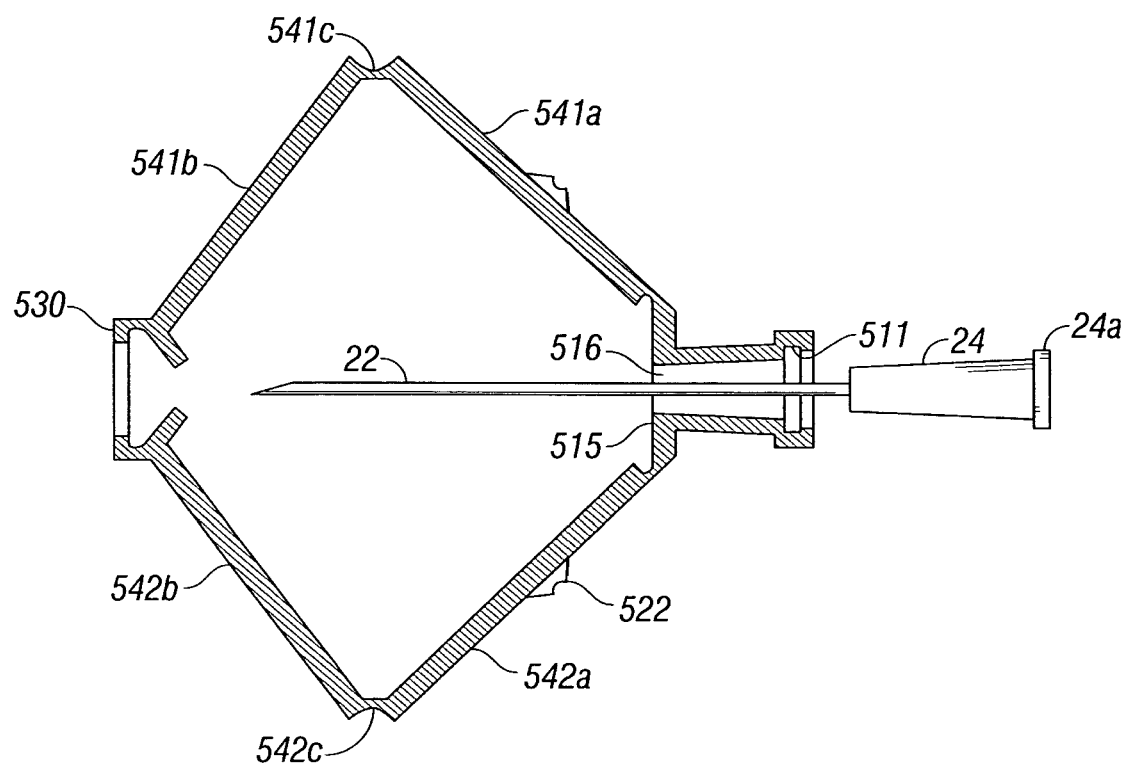
Figure 5F:
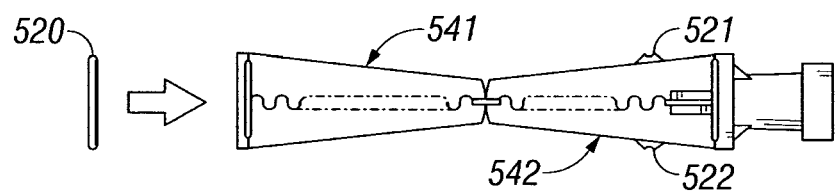
Figure 5G:
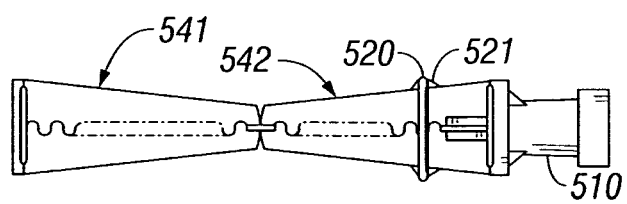

FIG. 3c schematically illustrates the syringe assembly shown in FIG. 3a during use whilst an injection is being given;

FIG. 3d is a perspective view of the assembly of FIGS. 3a to 3c in the position which it adopts after completion of an injection;

FIG. 4a is a perspective view from the front and one side of a safety device according to a fourth embodiment having two protective lockable side arms extending along the length of the device;

FIG. 4b is a perspective view from the rear and the other side of the device shown in FIG. 4a;

FIG. 4c is a cross-sectional view of the device of FIGS. 4a and 4b along the line cc of FIG. 4b;

FIG. 5a is a perspective view of a safety device according to a fifth embodiment in which pivoted locking arms extend along the length of the device;

FIG. 5b is a schematic cross-sectional view of the safety device of FIG. 5a along the line b-b in the safe position of FIG. 5a;

FIG. 5c is a schematic cross-sectional view of the safety device of FIG. 5a along the line b-b in a primed position;

FIG. 5d is a schematic cross-sectional view of the safety device of FIG. 5a along the line b-b in an injection position;

FIG. 5e is a schematic cross-sectional view similar to FIGS. 5b to 5c showing the safety device in the position in which it is moulded and a needle and needle-luer combination, illustrating how the combination is mounted into the safety device;

FIGS. 5f and 5g are schematic plan views of the safety device of FIGS. 5a to 5e illustrating how an elastic band is mounted on to the safety device.

FIG. 6a is a schematic, exploded, cross-sectional view of a sub-assembly of a safety device and a needle and needle-luer combination according to a sixth embodiment in which a bayonet type locking mechanism is employed;

FIG. 6b is a schematic cross-sectional view of a sheath portion forming part of the safety deice of FIG. 6a taken along the line b-b; and FIG. 6c is a schematic, cross-sectional view of the safety device shown in FIG. 6a in an assembled, safe, storage position.

FIRST EMBODIMENT

FIGS. 1a to 1f show a hypodermic syringe, needle and safety device assembly 1 according to a first embodiment. As shown, the assembly 1 comprises a syringe 10, a needle and needle-luer combination 20 and a safety device 100. The syringe 10 comprises a plunger 12, a fluid holding cylinder 14 and a syringe-luer portion 16. The needle and needle-luer combination 20 comprises a needle 22 and a needle-luer 24 for allowing the needle 22 to be easily mounted onto the syringe-luer portion 16. The needle 22 has a base 22a by which the needle 22 is attached to the needle-luer 24, and a chamfered point 22b (shown in FIG. 1c) for piercing the skin of the patient 180 to be injected. It is the chamfered point 22b which should be securely covered at all times, other than when a controlled injection is occurring, to prevent accidental needle stick injuries or contamination of the needle 22.

The needle-luer 24 is generally frusto-conical and is tapered from a syringe fitting end to a needle fitting end. The syringe fitting end is designed to fit onto the syringe-luer portion 16 and, in the present example, is sufficiently accurately manufactured and resilient that when it is driven over the syringe portion 16, it sealingly engages around the portion 16 in an interference fit. The needle fitting end has an internal diameter which is just larger than the external diameter of the base of the needle which it is to receive. To mount the needle, it is driven (base first) into the needle fitting end of the luer and then glued in place using a glue which is hard-cured to hold the needle securely in place. Once, the needle and needle-luer combination 20 is securely fitted onto the syringe 10, fluids may pass through the needle-luer 24 between the syringe 10 and the needle 22 without leakage at either end of the needle-luer 24. The needle-luer 24 also includes a small, radially outwardly protruding circumferential ring 24a formed around its base which assist gripping of the luer 24 when removing the luer 24 from the syringe 10. Needle-luers 24 of this type are well-known in the art of needle manufacture and will not be described here in greater detail.

The safety device 100, in the present embodiment, comprises a needle receiving portion, such as, for example, a needle-luer fitting portion 110, a nose portion 130, a first resilient means, such as, for example, a zig-zagging leaf spring or bellows portion 120 (hereinafter referred to as the spring 120) which is attached at one end to the needle-luer fitting portion 110 and at its other end to the nose portion 130 for biasing the nose portion 130 away from the needle-luer fitting portion 110. Also attached to the nose portion 130 is a locking means, such as, for example, a locking lever 140 which extends away from the nose portion 130 over the spring 120, the needle-luer fitting portion 110 and part-way over the syringe 10. Where the locking lever 140 passes over the needle-luer fitting portion 110, it passes through two upstanding locking arms 150, 160.

Figure 1E:
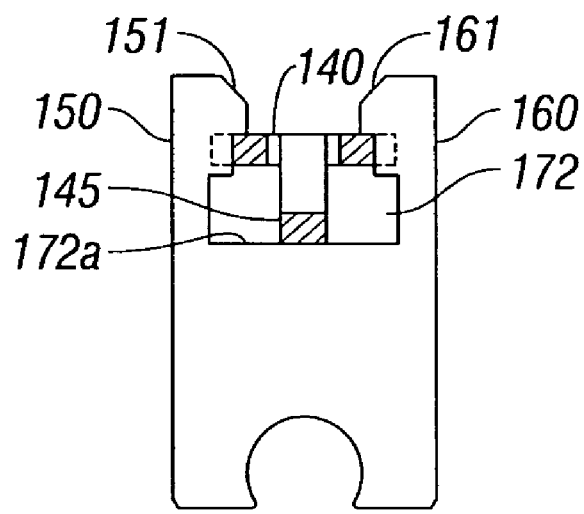
FIG. 1e is a cross-sectional view of the safety device forming a part of the assembly of FIG. 1a along the line e-e showing details of a locking arrangement in the storage position.
Figure 1F:
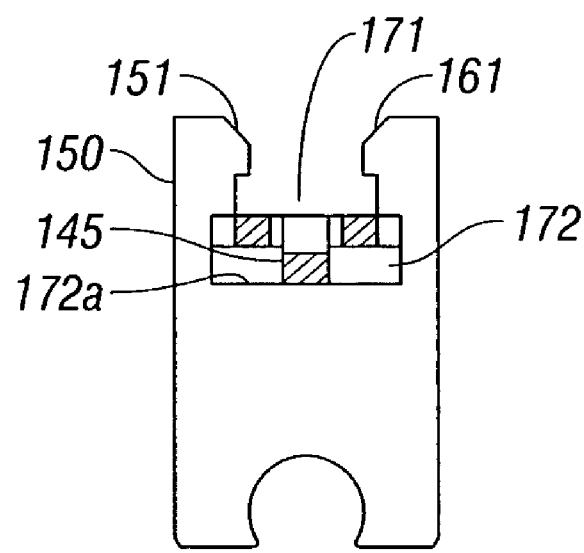
FIG. 1f is a cross-sectional view of the safety device forming a part of the assembly of FIG. 1b along the line f-f showing details of the locking arrangement in the primed position.
Figure 1G:
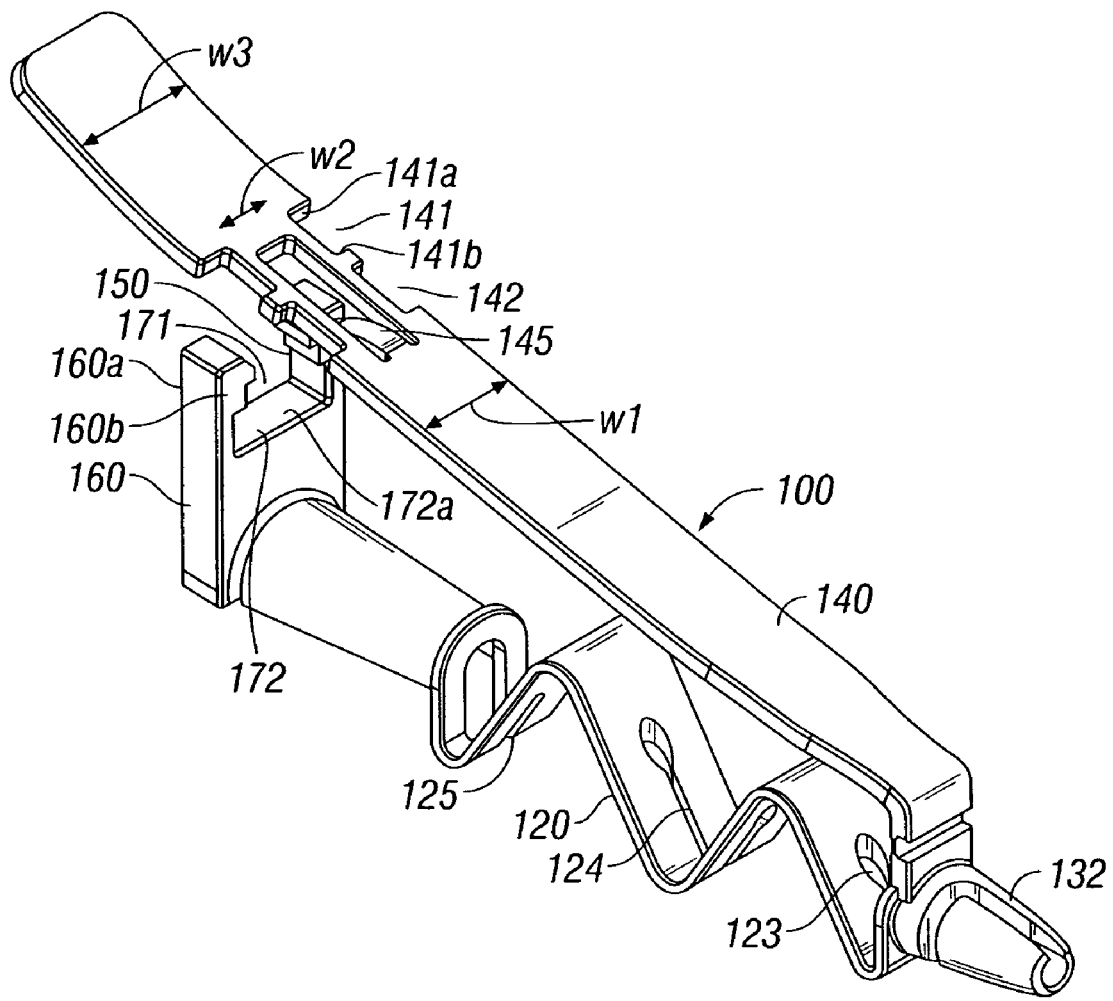
FIG. 1g is a perspective view of the safety device of the assembly of FIGS. 1a to 1f, showing in particular the details of the locking mechanism, prior to a snap assembly of the safety device.

As shown more clearly in FIGS. 1e and 1f, the locking arms are stepped on the inside to provide a first rectangular aperture 171 and a second rectangular aperture 172, underneath the first aperture, which is wider than the first aperture 171. As can be seen most clearly in FIG. 1g, which is a perspective view of the safety device 100 without the needle and needle-luer combination 20 and without the syringe 10, the locking lever 140 has first 141 and second 142 indented portions which have a width w2. In front of the second indentation 142 and between the first and second indentations 141, 142 the lever 140 has a width w1 which is greater than w2. Behind the first indentation 141, the lever 140 has a width w3 which is greater than both w1 and w2. The second stepped aperture 172 defined by the locking arms 150 and 160, has a width w1' which is just larger than width w1 to permit the front part of the locking lever 140 to slide therethrough but which is just smaller than w3 to prevent the back part of the locking lever 140 from sliding therethrough. The first aperture 171 has a width w2' which is smaller than the widths w1 and w3 along the front and back parts of the locking lever 140 but just wider than the width w2 of the indented portions 141, 142 to permit the locking lever 140 to slide upwardly into the first aperture 171 whenever either of the indented portions 141, 142 is in registry therewith. The locking lever 140 also includes a second resilient means, such as, for example, a sprung tongue 145 (which can be seen most clearly in FIG. 1g) which is located just in front of the second indented portion 142 and extends backwardly and downwardly to a point underneath the first indented portion 141. The sprung tongue 145 is operable to engage with the floor 172a of the second aperture 172 as the indented portions slide through the second aperture 172 to urge the locking lever 140 upwards in the direction of the first aperture 171.

When the safety device 100 is in its storage position as shown in FIG. 1a, the first indented portion 141 is locked within the first aperture 171. In this position, the locking lever 140 is prevented from sliding forwards or backwards through the first aperture 171 because the forward facing walls 141a of the first indented portion 141 engage with the backwards facing walls 150a, 160a of the arms 150, 160 and the backwards facing walls 141b of the first indented portion 141 engage with the forward facing walls 150b, 160b of the arms 150, 160.

Although the locking lever 140 may be relatively easily rotated about a pivot region 143 adjacent to where it attaches to the nose portion 130 to permit the user of the device to press the lever 140 down into the second aperture 172 from the first aperture 171, it is substantially rigid along its length between the indented portions 141, 142 and the pivot region 143. As a result, the nose portion is locked in position over the needle point 22B and will not move forwards or backwards as a result of a reasonable forwards or backwards force being applied to the nose portion 130 such as might happen as a result of an accidental nudge etc. (any such forces are transmitted from the nose portion 130 via the locking lever 140 and the needle-luer fitting portion 110 to the needle-luer 24 without requiring the needle 22 to transmit any such forces). Also, the nose portion 130 is held relatively stably against oblique forces due to the relatively flat wide profile of both the locking lever 140 and the spring 120.

When a user of the assembly 1 wishes to expose the needle 22 (especially at its point 22b) to permit an injection or a similar operation such as drawing fluid from a vial or from a patient into the syringe 10 using needle 22, the user pushes down on the free end 144 of the locking lever 140 to prime the safety device 100. This pushes the locking lever 140 into the second wider aperture 172 in which the lever 140 may slide backwards. FIG. 1b shows the assembly 1 in this primed position.

By maintaining a small amount of downward pressure on the locking lever 140, it is prevented from slipping back-up into the first aperture 171 due to the force from the tongue 145. Whilst the lever 140 is maintained in the second aperture 172, the user may expose the needle 22 by pulling the locking lever 140 backwards (ensuring that it does not slip upwards into the first aperture 171 as the second indented portion 142 passes between the locking arms 150, 160). Alternatively, the user may simply press the nose portion against the surface 181 of the object to be injected (in the illustrated example a patient's arm 180), again ensuring that the lever 140 is not allowed to slip upwards as the second indented portion 142 passes underneath the first aperture 171. As the user continues to press against the patient's skin 181, the lever 140 continues to slide backwards through the locking arms 150, 160 and the nose portion 130 slides backwards at the same time to expose the needle 22 which may therefore pierce and, with continued pressing by the user, continue to travel into the patient's arm 180. This is the position shown in FIG. 1c.

Once the injection has been completed, the assembly 1 is pulled away from the patient's skin 181 (hereinafter referred to as the injection surface 181). As the needle is pulled out, the nose portion 130 automatically slides forward (due to the resilience of the spring portion 120) over the needle 22 so as to continue to locate the nose portion 130 against the injection surface 181. Shortly after the point 22b of the needle 22 has been fully withdrawn from the patient's arm 180 and is safely located back inside the nose portion 130, the second indented portion 142 of the locking lever 140 comes into registry with the first aperture 171. Provided the user is not at this stage applying downward pressure onto the lever 140, the lever 140 will automatically slip upwards into the first aperture 171 and engage with the locking arms 150, 160 to prevent further forwards or backwards movement of the lever 140 and thus also the nose portion 130 (relative to the needle 22). This is the position shown in FIG. 1d.

The second indented portion 142, located in front of the first indented portion 141, ensures that the spring 120 does not need to extend fully back to its original storage position in order to lock the lever 140, and thus the nose portion 130, in a safe position. This is useful because, in the present embodiment, the spring 120 is formed from plastics material which is susceptible to an effect known as "plastic creep". The effect of plastic creep is that if the spring 120 is stored for a long time in the same position, even if the spring 120 was initially under compression, the material slowly "creeps" and loses its memory of its original, longer equilibrium length and instead tends to adopt its stored length as its equilibrium length; eventually, the spring 120 ceases to be under compression at all and when released maintains its stored length rather than expanding towards its original equilibrium length. Therefore, if only a single indented portion were used, the spring 120 might not have enough energy to ensure that the lever 140 returns fully to the single indented portion against all frictional forces etc. resisting the return movement. However, by providing a means for accommodating plastic creep, such as, for example, a second locking indented portion 142 in front of the first locking position 141, the safety device can be guaranteed to work for a predetermined shelf life.

Manufacture of the First Embodiment

Figure 1H:
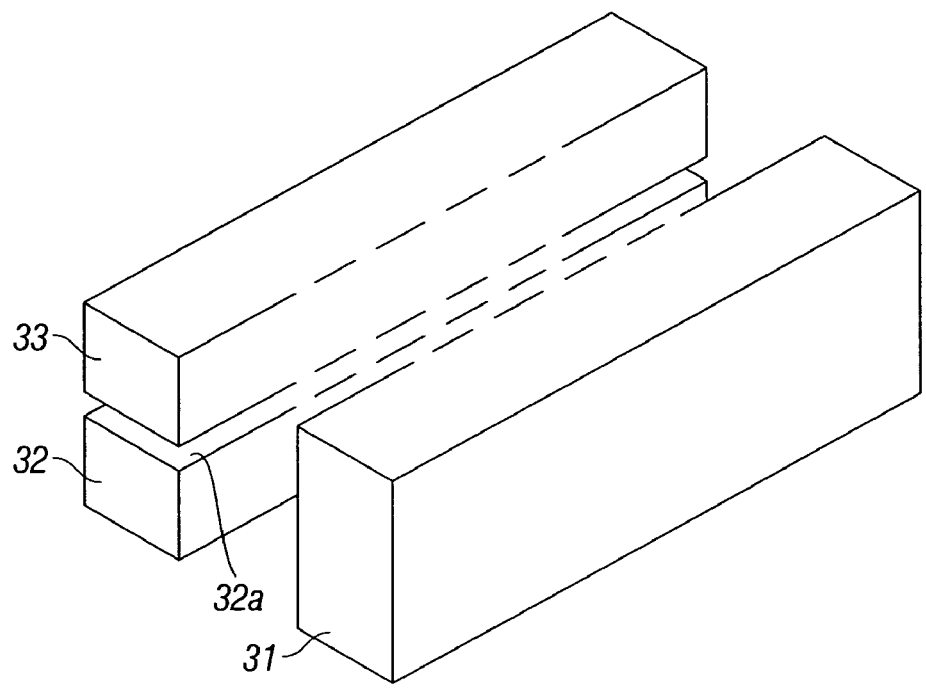
FIG. 1h is a schematic perspective view of the three mould blocks used to manufacture the safety device of FIGS. 1a to 1g.

FIG. 1h is a schematic perspective view of three mould blocks 31, 32, 33 for making the safety device 100 of assembly 1, showing how the mould blocks fit together, there being a base block 31 and first and second side blocks 32 and 33. The first and second side blocks 32,33 abut one another along a central joining plane with facing side faces 32a and then both of the side blocks 32,33 lie on top of the top surface of the base block 31.

Figure 1I:
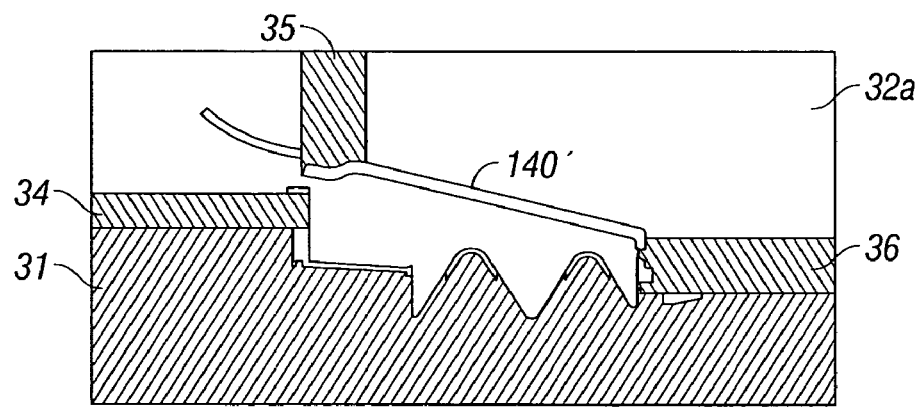
FIGS. 1i, 1j, 1k are cross-sectional views through the moulding tools used to manufacture the safety device of FIGS. 1a to 1g, including the mould blocks of FIG. 1h, taken through the plane in which two of the mould blocks of FIG. 1h abut one another, showing different stages in the disassembly of the moulding tools after formation of a safety device.
Figure 1J:
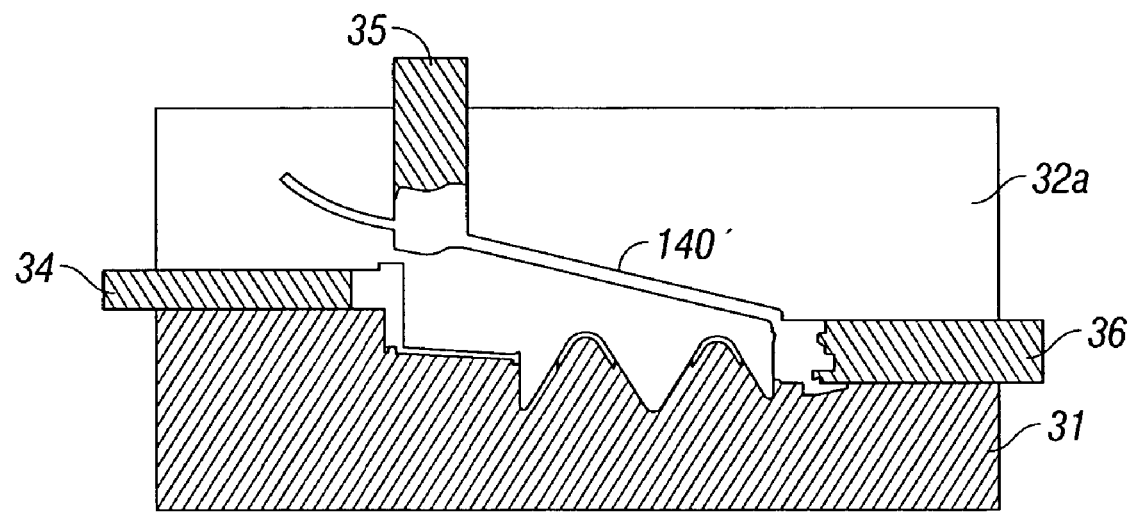
Figure 1K:
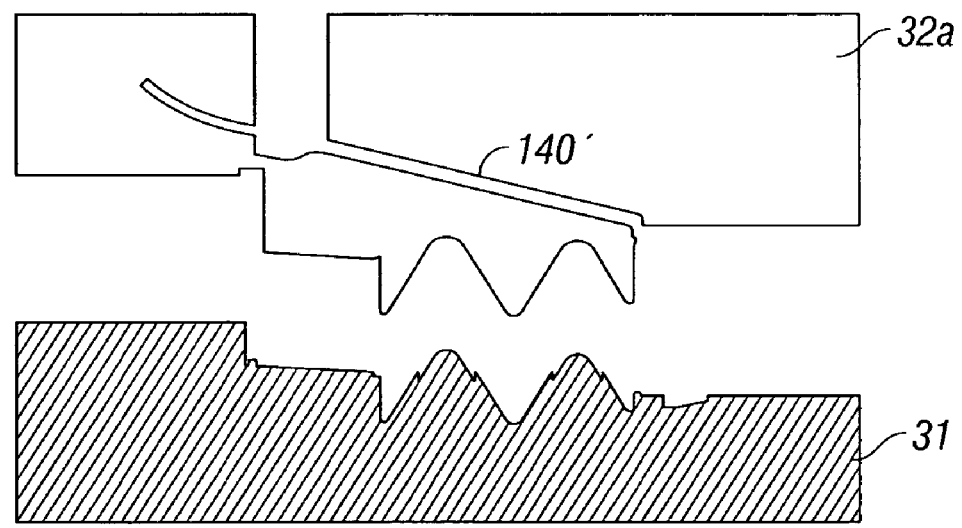

FIGS. 1i, 1j, and 1k are cross-sectional views through the central joining plane of the assembled mould blocks 31, 32, 33 together with mould inserts 34, 35, 36, such that the base block 31 and inserts 34, 35, 36 are seen in cross-section and the face 32a of the first side block 32 (which abuts against the facing side face of the second side block 33) is seen in plan view. The second side block 33 is not visible although the first and second side blocks 32, 33 are mirror images of one another reflected in the plane of their abutting surfaces 32a, such that a mirror image of FIGS. 1i, 1j and 1k would represent the same cross-sectional view but with the direction of view reversed and showing the corresponding face of the second side block 33 in place of the side face 32a of the first side block 32. FIG. 1i illustrates the mould tools 31 to 36 in the position they occupy when the plastic material is injected through an injection opening (not shown). FIGS. 1j and 1k illustrate how the inserts 34, 35 and 36 are firstly removed after moulding and then the mould blocks 31, 32, 33 are separated, firstly by separating the base block 31 from the two side blocks 32 and 33 and then separating the side blocks from one another. After separating the side blocks 32, 33, the moulded safety device 100 remains projecting out of one of the side blocks and may be easily ejected therefrom.

The process is then repeated by reassembling the mould tools 31 to 36 in the reverse order to which they were separated, and then injecting the mouldable material such as polypropylene, polyethylene or acetal (heated to the point where it becomes plastic) into the thus formed cavity. The injected material flows around the cavity to fill it completely and then is allowed to cool briefly. It will be apparent to a person skilled in the art that the grooves 140' and surface reliefs of the mould tools are exactly shaped to form the cavity with a shape which corresponds to the safety device 100. For example, groove 140' within the first side block 32 will form half of the locking lever 140 of the safety device 100 when moulded, while a corresponding groove in the second side block 32 will form the other half of the locking lever 140.

FIG. 1l is a perspective view of the nose portion 130 of the safety device 100 as soon as it has been removed from the mould tools 31 to 36. The first assembly operation is to attach the conventional needle and needle-luer combination 20 to the safety device 100. This operation is most clearly seen with reference to FIG. 1l together with FIG. 1m which is a cross-sectional view along the length of the safety device 100 as it comes out of the mould and FIG. 1n which is cross-sectional view of the safety device 100 shown in FIG. 1m along the line n-n. The combination 20 is supported in a vertical position and slid into a twisted slot 132 formed within the nose portion 130. A first part 132a of the slot 132 is vertical and extends from the side of the nose portion 130 towards the centre of the nose portion 130. Towards the centre of the nose portion 130, slot 132 twists to form a second part 132b which extends forwardly towards the nose end along the top of the nose portion 130 and a third part 132c which extends backwardly away from the nose end along the bottom of the nose portion 130. Corresponding slits 123, 124 and 125 are formed in the lower portions of the spring 120 in registry with the backwardly extending part 132c of the slot 132.

The slots 132c, 123, 124, 125 formed behind the vertical part of slot 132, are, as best seen in FIG. 1n, tapered in a radially inward direction towards central axial holes 132d, 123a, 124a, 124b and 125a (see FIGS. 1n and 1o), which have a diameter d3, which is just larger than the diameter d2 of the needle 22, to hold the needle 22 in place when it is located in the central axial holes. The width d1 of the smallest parts of the slots 132c, 123, 124, 125 is just smaller than the diameter d2 of needle 22 such that a snap-fit action is required to press the needle through the slots and into the central axial holes.

Having slid the combination 20 vertically into the slot 132 from a sideways direction to arrive at the position shown in FIG. 1m, the needle combination 20 is then twisted in a clockwise direction through ninety degrees to bring the needle point 22b pointing forwards (towards the nose end of the nose portion 130) and the needle-luer 24 into engagement with the needle-luer holding portion 110. In a similar fashion to the slots 132c, 123, 124, 125, the needle-luer holding portion 110 has a "c" shaped profile with an entrance which is slightly narrower than the needle-luer 24 to provide a snap fit whereby the needle-luer 24 may be pressed into the holding portion 110 from underneath by applying a moderate pressure, but may not be easily removed from portion 110.

Figure 1O:
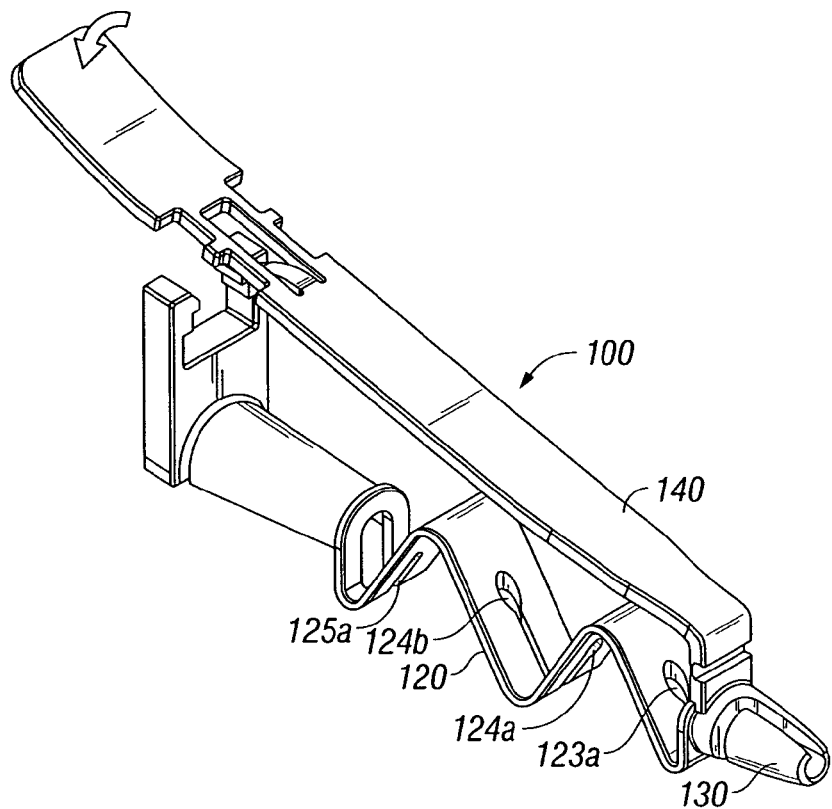
FIG. 1o is a perspective view of the safety device of FIGS. 1l to in prior to a snap assembly stage.
Figure 1P:
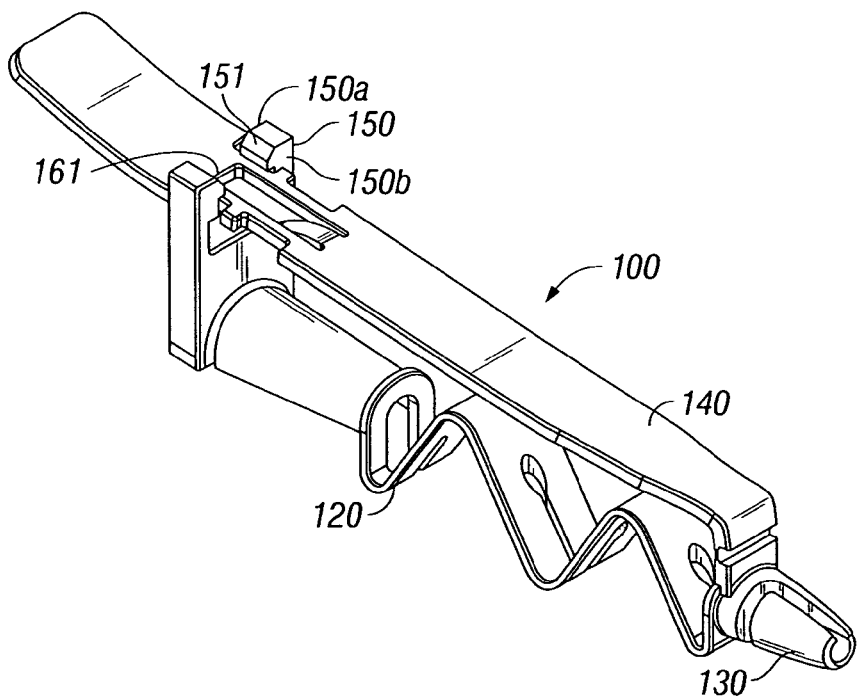
FIG. 1p is a perspective view of the safety device of FIGS. 1l to 1o after the snap assembly stage.

The next assembly step is to press the locking lever 140 down into the first aperture 171 as illustrated in FIGS. 1o and 1p which are perspective views of the safety device 100 after moulding. The camming surfaces 151, 161 assist in this since the throat between the bottom of the two camming surfaces 151, 161 is narrower than the width w2 of the first indented portion 141, unless the locking arms are flexed outwardly. However, the action of the first indented portion 141 being pressed downwardly through the arms 150, 160 causes the edges of the indented portion 141 to press against the camming surfaces 151, 161 which in turn causes the arms 150, 160 to flex outwardly, permitting the indented portion 141 to snap into place into the first aperture 171. At this point the arms 150, 160 flex back into an upright position effectively holding the indented portion 141 in place in the first aperture 171.

The final assembly step to arrive at the assembly 1 of FIGS. 1a to 1d involves the mounting of the subassembly of the safety device 100 and the needle and needle-luer combination 20 onto the syringe luer portion 16 of the syringe 10 (shown in FIG. 1a). This step can either be performed within the needle manufacturing factory as with the previous steps to form fully assembled syringe plus needle assemblies 10, 20, 100 for shipping, or the subassemblies (of needle and needle-luer combination 20 and safety device 100) may be boxed and shipped in their current form for later assembly onto a syringe by a user. In both cases, each individual assembly 10, 20, 100 or subassembly 20, 100 is first placed into a sterile sealed bag prior to boxing and shipping. Note that neither the assemblies nor the subassemblies require a plastic cap to cover the needles (as is the case with prior art hypodermic needle assemblies) since the needles 22 are protected and safe by virtue of the safety device 100. In the case where subassemblies 20, 100 are shipped without attached syringes, each such subassembly 20, 100 may be mounted by a user onto the syringe luer portion 16 of a syringe 10 immediately prior to its being used, in much the same way as a conventional needle and needle-luer combination 20 may be mounted by a user onto the syringe-luer portion 16 of the syringe 10 immediately prior to its being used, the only difference being that in the conventional case a plastic cap which is used to protect the needle during storage is removed by the user immediately after fixing the needle-luer onto the syringe-luer portion 16. In the present example, the needle-luer 24 is a force fit type attachment to the syringe-luer portion 16 and simply needs to be pressed onto the syringe-luer portion 16 until it is firmly attached thereto.

Discussion of the First Embodiment

The safety device 100 of the first embodiment is very convenient because it may be manufactured in bulk as a single one piece injection moulded plastics product and a simple assembly permits a conventional needle and needle-luer combination 20 to be mounted safely within the safety device 100 with very little risk of the needle point 22b (especially the chamfered part) being scratched or becoming compromised by contact with a surface of the safety device (if the chamfered part is scratched causes an injection made with the needle to be more painful). Furthermore, as soon as the needle and needle-luer combination 20 has been mounted within the safety device 100, the subassembly 20, 100 is safe and does not require a protective plastic cap for storing and transporting the needle and needle-luer combinations 20. However, alternative embodiments are possible which although not being formed from a single piece of injection moulded plastics material, are still relatively easy and cheap to manufacture and assemble. The second embodiment described below is an example of a safety device having two components.

SECOND EMBODIMENT

Figure 2:
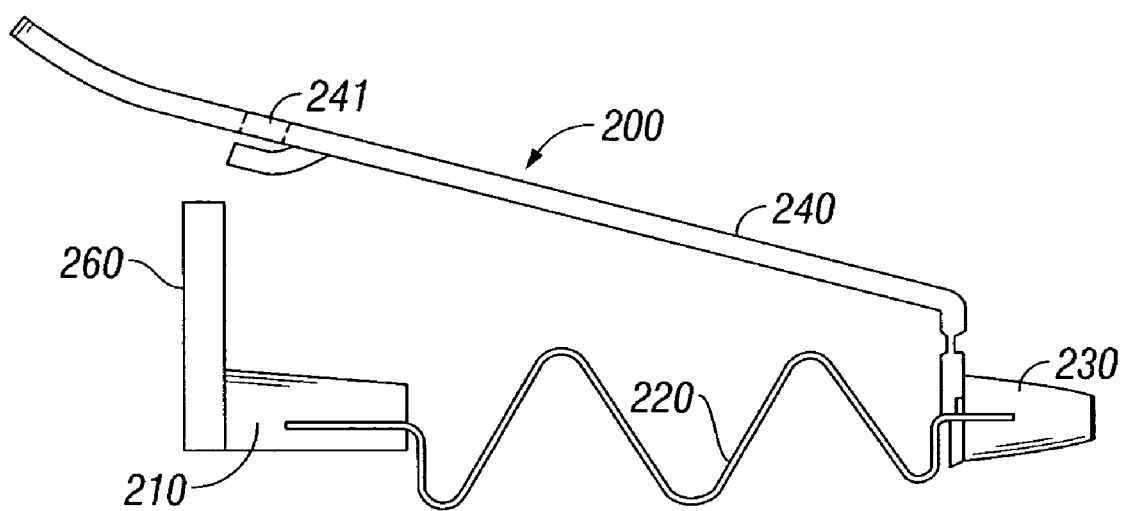
FIG. 2 is a cross-sectional view of a safety device according to a second embodiment, which shows how a metallic spring has been outsert moulded into the safety device.

FIG. 2 shows a safety device 200 according to a second embodiment in which the plastics spring 120 of the safety device 100 according to the first embodiment has been replaced with a first resilient means, such as, for example, an outsert moulded metal spring 220. The metal spring 220 is attached to the remainder of the safety device 200 at its ends which are encased with the injection moulded plastics material. In order to manufacture the safety device 200, similar mould tools to those used to manufacture the first embodiment may be used except that the mould blocks have slightly thinner grooves where the metal spring element 220, which is slightly thinner than the plastic spring 120, is to be mounted, such that it is held securely during the injection process. The metal spring 220 is preformed by any suitable process to resemble the central part of the plastic spring 120 (apart from being slightly thinner as mentioned above) of the first embodiment. In particular, the metal spring 220 also includes slits formed within its lower trough portions to permit a needle to pass through the slots into the final position of the needle extending from the nose portion to the needle-luer holding portion.

In the second embodiment, the locking lever only requires a single indented portion 241 since the metal spring 220 will not suffer from plastic creep. In this embodiment, the indented portion 241 is located slightly in front of the location along the locking lever which would engage with the locking arms if the locking lever were pressed down towards the arms without first extending the spring portion 320 to place it under tension. Thus, in order to snap assemble the safety device 200, the lever 240 is first pulled backwards compressing the spring 220 until the indented portion 241 is in registry with the aperture between the upright arms 260 and then the lever is snapped into place into the first aperture. Because the metal spring portion 320 does not suffer from plastic creep, when the safety device 300 is used, the metal spring portion 320 has enough energy as a result of the initial tension given to it (during the snap assembly) to ensure that the device 200 returns into the safe locked position.

THIRD EMBODIMENT

FIG. 3a is a perspective view of an assembly 3 according to a third embodiment. The safety device 300 of the third embodiment is similar to the safety device 100 of the first embodiment except that in place of a bellows spring portion 120 having slots formed therein to permit the needle 22 to pass through the middle of the spring portion, a single turn leaf spring portion 320 is provided between the nose portion 330 and the needle-luer attachment portion 310 which extends over the top of a locking lever 340. A similar locking mechanism (described in greater detail below) to that provided in the first embodiment is employed and FIGS. 3b, 3c and 3d show the assembly 300 in the first safety (storage) position, the position which it adopts during an injection and the second safe position which it adopts immediately after an injection respectively. From these Figures, it can be seen that, in use, the single turn leaf spring 320 arches upwardly while the injection takes place. Upon completion of the injection, the spring portion 320 drives the nose portion 330 away from the needle-luer mounting portion 310 until the second locking position of the locking lever 340 is reached whereupon the safety device 300 locks into the second safe position.

In the present embodiment, the locking mechanism comprises: the locking lever 340 in which are formed first and second upwardly projecting barbs 341, 342 and a downwardly projecting barb 343; an aperture 371 formed within a stiff connecting portion 370, which rigidly connects one end of the spring 320 to the needle-luer fitting portion 310; and an "L" shaped leaf spring 372 which urges the locking lever 340 upwardly (so as to urge the locking lever into engagement with the upper surface of the aperture 371). In the first safe position (as shown in FIGS. 3a and 3b), the first upwardly projecting barb 341 engages with the forward facing wall 370a of the stiff connecting portion 370 immediately above the aperture 371, to prevent backwards movement of the locking lever 340 (and hence also of the nose portion 330). Also in the first safe position, the downwardly projecting barb 343 engages with the leaf spring 372 to prevent forwards movement of the locking lever 340 (and hence also of the nose portion 330). In order to prime the device 300 to allow an injection to take place, the user presses down on the locking lever 340 against the bias of the leaf spring 372 to a position where the first upwardly projecting barb 341 is clear of the forward facing wall 370a and may pass through the aperture 371. With the lever held in this position, the nose portion 330 is pressed against the injection surface 181 causing the nose portion 330 and the locking lever 340 to slip backwards relative to the needle to allow the injection to take place. The user must ensure that the locking lever 340 continues to be pressed downwardly against the bias of the leaf spring 372 while the second upwardly projecting barb 342 clears aperture 371. When the injection has finished, the needle is retracted from the object 180 and the spring 320 automatically drives the nose portion forward relative to the needle and thus also the locking lever 340 forwardly through the aperture 371. The forward facing surfaces of the upwardly projecting barbs 341, 342 are angled to provide a camming surface such that when the second upwardly projecting barb 342 comes into contact with the upper surface of the aperture 371, the force of the spring 320 driving the locking lever forwardly through the aperture causes the locking lever 340 to deflect downwardly against the bias of the leaf spring 372 as the camming surface of the second upwardly projecting barb 342 passes underneath the top surface of the aperture 371. Once the second upwardly projecting barb 342 has been cleared in this way, the device 300 is safe since the locking barb 342 will not pass back underneath the upper surface of the aperture 371 in a backwards direction unless an actuating force is applied against the bias of the leaf spring 372 by the user. Thus, even if the spring 320 does not have sufficient energy to return the safety device to the first safe position (i.e. the storage position) by driving the first barb 341 through the aperture in a similar way, the safety device 300 is none-the-less safeguarded against accidental needle stick injuries.

Manufacture of the Third Embodiment

In order to manufacture the safety device 300, it is firstly moulded in a position in which the locking arm does not project through the aperture 371. When the device 300 comes out of the mould, the first step is to bend the spring 320 and needle-luer fitting portion 310 relative to the locking lever 340 and to fit the locking lever 340 through the aperture 371. The downwardly projecting barb 343 has an angled backward facing surface which forms a camming surface which allows it to press down leaf spring 372 as it passes backwardly past it. Thus the locking lever 340 is driven through aperture 371 until the downwardly projecting barb 343 has cleared leaf spring 372 and then the device 300 is in its first safe (storage) position. Note that in this embodiment, the width w1 of the locking lever 340 is substantially constant along its length and is narrower than the internal width of the aperture 371 to permit it to slide therethrough except when prevented from doing so by the barbs 341, 342, 343.

The next step is to fit a conventional needle and needle-luer combination 20 into the safety device 300. This is done by driving the combination point first forwardly through the needle-luer fitting portion 310 until the needle point 22b is securely located within the nose portion 330 and the needle-luer 24 snaps into place in the needle-luer fitting portion 310. The needle-luer fitting portion 310 includes a groove in which the rim 24a of the needle-luer 24 locates to provide secure axial location of the combination 20. The needle-luer fitting portion also has an "S" shaped split (not shown) along one of its sides to permit the fitting portion 310 to flex open to receive the needle-luer 24 and to provide interlocking rounded teeth which securely hold the needle-luer 24 in place.

FOURTH EMBODIMENT

FIG. 4a is a front perspective view from one side of a safety device 400 according to a fourth embodiment, FIG. 4b is a rear perspective view from the other side of the safety device 400 and FIG. 4c is a cross-sectional view taken along the line c-c in FIG. 4b. The safety device 400 is similar to the safety device 300 of the third embodiment but includes two additional side arms 441, 442 which extend between the nose portion 430 and the needle-luer fitting portion 410. As most clearly shown in FIG. 4c, the bottom portions of the side arms 441, 442 curve inwardly and abut one other along a central plane of the device 400 to completely enclose the needle 22 when fitted. A stiffening tunnel 470 is provided between the luer fitting portion 410 and the spring 420 (which is rigidly attached to the top surface of the tunnel 470). When assembled, the locking lever 440 extends from the nose portion 430 through the tunnel 470 to a user actuable end portion thereof. Additionally, the side arms 441, 442 have semicircular locating tabs 441a, 442a which locate within semicircular indentations 481, 482 formed within the side walls of the tunnel 470 to inhibit vertical movement of the side arms relative to the side walls of the tunnel 470 when in a safe locked position.

The device 400 is moulded with the locking lever 440 and side arms 441, 442 away from the tunnel 470, and the first assembly stage is to pass the locking lever 440 through the tunnel 470 into the safe position shown in FIGS. 4a and 4b. The second step is then to pass the needle and needle-luer combination 20, point first, through the frusto-conical needle-luer fitting portion 410 until the rim 24a of the needle-luer 24 is pressed into snap fit engagement with a co-operating groove 411 formed within the needle luer fitting portion 410. During this process care must be taken not to touch the point 22b of the needle 22 especially when the needle point passes through the small hole 432 formed in the back face 431 of nose portion 430 (as shown in FIG. 4c).

The locking mechanism by which locking lever 440 locks into a first narrow aperture 471 located above a second wider aperture 472 within the tunnel 470 when an indented portion 440a of the locking lever 440 comes into registry therewith is substantially the same as in the first embodiment (although in this embodiment there is only a single indented portion 440a and no mechanism for accounting for plastic creep). However, in addition, the locking lever 440 includes a wedge mechanism (not shown) which acts to push the side arms 441, 442 away from the locating surfaces of the indentations 481, 482 of the side walls of the tunnel 470 as the locking lever 440 is pushed down by a user, against the action of a sprung tongue (not shown), into the second lower wider aperture 472 and thus into a primed position. After an injection has taken place, the locking lever 440 is urged back through the tunnel 470 along the wider aperture 472 by the action of the spring 420 until the indented portion 440a comes into registry with the first aperture 471 of the tunnel 470, whereupon the locking lever is urged upwardly back into the first aperture 471; at the same time, the side arms 441, 442 slide back radially inwardly to locate against one another's bottom edges and to locate the backwards facing edges of the semicircular tabs 441a, 442a against the forward facing edges of the indented portions 481, 482. The safety device is then back in its safe position.

FIFTH EMBODIMENT

FIG. 5a is a perspective view from the front and to one side of a safety device 500 according to a fifth embodiment. FIGS. 5b, 5c and 5d are cross-sectional views of the safety device 500 taken along the line b-b of FIG. 5a, in a safe position, a primed position and an injection position respectively.

The safety device 500 includes a luer fitting portion 510 for receiving a needle-luer 24, first and second locking arms 541, 542 for protectively surrounding a needle 22, and a nose plate 530 having an aperture 531 formed therein for permitting the end 22b of the needle 22 to project therethrough during an injection. Each of the locking arms 541, 542 is split into a back half 541a, 542a and a front half 541b, 542b. Each back half 541a, 542a is pivotally connected to its respective front half 541b, 542b by means of upper 541c, 542c and lower 541c', 542c' (see FIG. 5b) pivoting joining regions. The profile of each arm is semi-elliptical tapering radially inwardly towards the joining regions. Each arm 541, 542 pivotally attaches at its back end to a back plate 515 by means of vertical hinge regions 541d, 542d. The back plate 515 is rigidly attached to the luer fitting portion 510 and has an aperture 516 (see FIG. 5e) formed therein for permitting the needle 22b to pass therethrough. The hinge regions 541d, 542d are formed at the edges of the back plate 515 to provide a distance between the hinge regions 541d and 542d which is approximately one quarter of the length of each arm 541, 542. Similarly, the front ends of the arms 541, 542 are pivotally attached to the nose plate 530 at its edges by means of vertical hinge regions 541e, 542e, which are similarly spaced apart from one another (in a radial direction).

The upper and lower facing edges of the arms 541, 542 are shaped, when viewed from above and below respectively, to provide rounded interlocking teeth (represented in FIG. 5a by the sinusoidal line 543). The facing edges of each arm which abut against one another when in the closed safe position shown in FIG. 5a, have a depth of approximately 5 percent of the overall length of the device 500 to ensure that they locate securely against one another. In the present embodiment, the locating edges are flat for ease of moulding.

Formed on top of each arm, 541, 542, towards the back inside edge of each, is a first 540b and second 540a half of a priming button 540, which, when pushed forwards by a user, causes the back halves 541a, 542a of the locking arms to pivot outwardly about the hinge regions 541d, 542d.

The safety device 500 also includes an elastic band 520 which is mounted around the back halves 541a, 542a of the locking arms 541, 542 to bias the locking arms together into the safe position shown in FIG. 5a. The elastic band 520 is held in place by means of first and second securing lugs 521, 522 formed on the outer edges of the first and second arms, 541, 542 respectively.

Referring now to FIGS. 5b, 5c and 5d, when the subassembly of safety device 500 and a conventional needle and needle-luer combination 20 is in the safe position shown in FIG. 5b, the subassembly is secure against accidental needle stick. In particular, when in this position, a force applied onto the nose plate 530 will tend to be transmitted via the pivot regions 541e, 542e, 541c,c', 542c,c', 541d, 542d, which, because of the "X" shape formed by these force lines, tends to push the locking arms 541, 542 against one another holding the arms securely in place together and preventing any relative movement between the nose plate 530 and the needle 22. In this position, the structure formed by the locking arms is very stable and will also resist torsional forces etc. which may be applied to the safety device 500.

In order to enable an injection to take place, a user of the device must first prime the safety device 500 into the primed position shown in FIG. 5c. To do this, the user holds a syringe (not shown in FIG. 5c) to which the needle-luer 24 is attached and at the same time pushes the actuating button 540 forwards (i.e. towards the nose piece 530). This action causes the locking arms to pivot outwardly against the bias of the elastic band 520 into the primed position illustrated in FIG. 5c. In this position, the middle pivoting regions 541c, 541c', 542, 542c' are located further apart from one another in the widthwise (horizontal radial) direction than the pairs of pivoting hinges formed at the back and front of the arms respectively. In this position, if a backwards force is applied to the nose plate 530, this force will tend to push the central joining regions 541c, 542c further apart from one another against the bias of the elastic band 520. Thus, once the subassembly has been placed into the primed position shown in FIG. 5c, the user may press the nose piece 530 against an injection surface and by applying continued pressure will cause the locking arms to pivot further and further outwards driving the nose piece 530 backwards over the needle and allowing the needle to enter the object to be injected. This is the position shown in FIG. 5d.

Upon completion of an injection, as the needle and needle-luer combination 20 is pulled away from the injection surface, the biasing elastic band 520 biases the locking arms towards one another which in turn causes the nose piece 530 to continue to locate against the injection surface until the needle 22 is completely withdrawn from the injection surface at which point the locking arms 541, 542 snap back together into the safe locked position shown in FIGS. 5a and 5b.

Manufacture of the Fifth Embodiment

In order to manufacture and assembly the subassembly of the safety device 500 and a needle and needle-luer combination 20, they safety device 500 is first moulded as a single injection moulded piece (apart from the elastic band 520) in the position shown schematically in FIG. 5e. A needle and needle-luer combination 20 is then mounted into the safety device 500 by pushing the needle combination 20 (needle point 22b first) through the needle-luer receiving portion 510 in the forward direction until the needle-luer 24 snaps into position within the needle-luer receiving portion 510. Rim 24a locates within groove 511 (FIG. 5e). Having fitted the needle and needle-luer combination 20 in this manner, the locking arms 541, 542 are then closed into the locked position shown in FIG. 5f and thereafter the elastic band 520 is mounted around the arms 541, 542 as shown in FIG. 5g.

SIXTH EMBODIMENT

FIG. 6a is an exploded cross-sectional side view of a subassembly of a safety device 600 and needle and needle-luer combination 20 according to a sixth embodiment. The device 600 includes a substantially cylindrical needle-luer fitting portion 610, a metal helical spring 620 and a sheath cylinder 630.

In this embodiment, the needle-luer fitting portion 610 comprises an outer substantially cylindrical portion 614 and an inner substantially frusto-conical portion 615. As shown, the two portions 614,615 are nested inside one another, co-axially, with the two portions being integrally connected together at the larger diameter end of the substantially frusto-conical portion 615; the substantially frusto-conical portion 615 is slightly longer than the substantially cylindrical portion such that its narrower end projects through the other end of the substantially cylindrical portion 614. In this embodiment, two radially outwardly projecting following pins 611,612 are formed on opposite sides of the substantially cylindrical portion 614 on sprung tongues which permit the following pins 611,612 to be deflected radially inwardly, against the bias of the sprung tongues, such that the ends of the following pins 611,612 lie flush with the outer surface of the substantially cylindrical portion 614.

The sheath portion 630 is substantially cylindrical and has an internal diameter which is just slightly larger than the outer diameter of the substantially cylindrical portion 614 of the needle-luer fitting portion 610, to permit the sheath portion 630 to slide telescopically over the needle-luer fitting portion 610. In the present embodiment, the sheath portion 630 has a first and second groove 631,632 formed within its inner surface which are sized to locate the first and second following pins 611,612 respectively. Each groove 631,632 includes an axially directed portion 631a, 632a and at the back end of each of these portions, a circumferentially directed portion 631b, 632b; as is described in greater detail below, the grooves 631, 632 co-operate with the following pins 611, 612 to provide a secure automatically biased, bayonet type locking mechanism.

In the present embodiment, each radially directed portion 631b, 632b of the grooves 631, 632 is formed by a slot which extends completely through the surface of the sheath 630; the axially directed portions 631a,632a of the grooves 631, 632 have the same radial depth and width as the circumferentially directed portions 631b,632b, however, as can most clearly be seen in FIG. 6b, which is a cross-sectional view through the line b-b of FIG. 6a (but not showing the spring 620), the thickness of the sheath walls surrounding these portions 631a,632a is increased such that these portions do not extend through the sheath walls as do the circumferentially directed portions 631b,632b.

First and second radially inwardly directed flanges 638, 639 are formed towards the front of the sheath 630. Each flange 638,639 has a first stepped part which extends perpendicularly away from the internal surface of the sheath 630 to act as stops which prevent the needle-luer fitting portion from sliding forward of these flanges, and a second portion which tapers radially inwardly and forwardly to provide a tapering surface against which the front end of the spring 620 may locate in an interference fit.

In order to assemble the sub-assembly 600,20. The back end of the spring 620 is secured around the outer surface of the substantially frusto-conical portion 615 of the needle-luer fitting portion 610 towards the front end thereof by means of an interference fit, and the spring 620 and fitting portion 610 are pushed forwardly into the sheath 630 until the front end of the spring 620 is secured within the inner surface of the sheath cylinder 630 against the tapering surfaces of the flanges 638,639.

At this point, the spring 620 is under compression so as to bias the sheath 630 forwardly relative to the needle-luer fitting portion; this assists in maintaining the spring 620 securely located at both its ends. To finish assembling the sub-assembly, the sheath 630 is twisted clockwise (when viewed in the backwards direction—ie from the point of the needle 22b to the needle luer 24) to generate a reverse-directed biasing torsion in the spring 620, then the following pins 611, 612 are deflected radially inwardly to permit their ends to pass inside the sheath 630 and the needle-luer fitting portion 610 is pushed further into the sheath 630 against the axially directed bias of the spring 620 until the following pins 611, 612 come into registry with the radially directed portions 631b, 632b of the grooves 631, 632, whereupon they snap radially outwardly into location within the grooves. Upon releasing the needle-luer fitting portion 610, it will twist, as a result of the torsional bias provided by the spring 620, in a clockwise direction (again when viewed in a backwards direction) relative to the sheath potion 630 until the following pins 611,612 reach the ends of the radially directed portions 631b,632b of the grooves 631,632 which are distant from the axially directed portions 631a,632a. Finally, the needle and needle-luer combination 20 is mounted into the needle-luer fitting portion 610, by passing the combination 20, needle point 22b first, through the back of the fitting portion 610 until the needle-luer 24 snaps into place with its rim 24a axially located within a co-operating groove formed in the fitting portion 610. This is the safe position shown in FIG. 6c.

In order to use the sub-assembly 20,600, a user mounts it onto a syringe (not shown) and then, in order to prime the safety device 600, the user twists the sheath cylinder 630 against the torsional bias of the spring 620 until the following pins 611, 612 come into registry with the axially directed portions 631a, 632a, of the grooves 631,632. The user then presses the sheath 630 against an injection surface and the sheath 630 will slide back over the needle 22 against the axially directed bias of the spring 620 with the following pins 611, 612 running up the axially directed portions 631a, 632a of the grooves 631, 632. As those skilled in the art will appreciate, the sheath 630 has an internal diameter which is sufficiently large to permit it to slide over the front of the syringe if necessary. Upon completion of the injection, as the needle 22 is withdrawn from the injection surface, the front end of the sheath 630 continues to press against the injection surface until the needle is fully withdrawn out of the injection surface. The sheath 630 continues to slide forwardly until the following pins 611,612 reach the back end of the axially directed portions 631a, 632a of the grooves 631, 632, whereupon the torsional bias of the spring 620 twists the sheath 630 back into the safe position shown in FIG. 6c.

Variations

A number of variations to the above described embodiments are envisaged. For example, in the above described embodiments, different shapes and configurations of springs and elastic bands are used, however these represent only a small sample of the different types of resilient means which could be used. For example, a plastic helical spring could have been employed in the sixth embodiment, in which case it would be possible to manufacture the device as a single injection moulded device. Alternatively, in the first embodiment a semi-helical spring formed from plastics material could have been used (by semi-helical is meant an arrangement in which a series of "V" shaped segments are linked together at their ends, with alternate segments being bent with oppositely directed curvatures such that each apex is connected to the other by a helical link, but adjacent apexes being radially separated from one another such that there is a clear, axially directed, gap between the apexes through which a needle may be passed).

Many different mechanisms for dealing with "plastic creep" could have been employed. In general, any mechanism which either permits the user to give the system some extra energy during priming of the device to enable it to easily return to the same safe position in which it is stored, or which permits the device to return to a second safe position to which the device requires less energy to return may be used. An example of the first type of mechanism could be a variation to the sixth embodiment in which a plastic helical spring is used; the spring can be arranged such that twisting the spring to prime the device affects the performance of the spring in the axial direction such that its compression is increased. This additional compression will ensure that the sheath returns axially as far as the radial portion of the groove. Even if the sheath does not make it to the end of the radial portion of the groove, the device will be safe so long as the following pins are not in registry with the axially directed portions of the grooves.

In the above described embodiments, there are two resiliently biased actions. Firstly a sheath portion is resiliently biased into one or more positions in which the point of the needle is protected and secondly a locking mechanism is resiliently biased into a locked position. These two actions combine to ensure that if the device ever leaves the control of a user (eg. if it is dropped) it will automatically return to a safe position. In some of the above described embodiments two separate resilient members are used to perform these two separate actions, however, more or fewer such members could be used as is done in the sixth embodiment where a single resilient member (spring 620) provides axial biasing to drive the sheath over the needle point and torsional biasing to drive the device into a locked position. Many other similar arrangements which perform these two functions may be used.

In the first embodiment, the safety device has only a single locking lever, however, more than one locking lever could be used instead. However, preferably at least one side of the device (generally referred to as the bottom of the device) is kept as clear as possible from outwardly projecting items such as locking arms or springs to prevent them from getting in the way of a user whilst giving an injection where the user wishes to pierce the injection surface at a small angle of incidence. Instead of priming the device by pushing down on the locking lever, the device could be arranged so that some other action was required by the user such as pushing the lever up or pulling it back. However, it is generally preferred that priming should be performed by squeezing radially inwardly or pushing axially forwardly an actuating member designed to be actuable by the thumb of a user's hand in which the syringe and device assembly is being held, for ease of use and ergonomic reasons.

The metal spring used in the second embodiment could be replaced by a metal spring having a different shape, such as, for example, a helical spring.

In the fifth embodiment, a single pivoted locking arm or three or more pivoted locking arms could have been used in place of the two described pivoted arms. Instead of having flat locating edge surfaces formed on the locking arms, tongue and groove co-operating surfaces could have been used to improve the location of the edges against one another at the cost of more difficult manufacturing. Also, instead of having a number of interlocking circular teeth formed along the locating edges to prevent axial slipping of the arms relative to one another when in their closed position, one or more such interlocking features could have been used and the interlocking features could have any shape such as triangular, etc. provided that they do not prevent the arms from opening when the device is primed by a user.

In the sixth embodiment, one following pin and co-operating groove could have been used in place of the two described pins and grooves. Alternatively, three or more such pairs of pins and co-operating grooves could have been used. Three pairs of equally circumferentially spaced pins and grooves is an especially useful arrangement for increasing the general strength of the locking mechanism as would be appreciated by a mechanical engineer.

Instead of providing a safety device which permits a conventional needle and needle luer combination to be mounted thereto, a safety device could be formed which includes a portion which performs the functions of a conventional needle-luer of enabling the base of a needle to be securely mounted thereto and of permitting the device to be securely attached to a syringe or catheter, etc. In such a case, the device can completely replace a conventional needle-luer and may be moulded as a single injection moulded device, thus reducing costs for the needle-manufacturer (although at the cost of requiring the needle manufacturer to alter its needle manufacturing process to recover needles prior to their being mounted onto a conventional needle-luer).

The safety device could also be manufactured to include the needle within the device, thus rendering the safety device as a complete needle and cap as opposed to simply being a safety sheath. This may be achieved by inserting the needle within a mould tool used to mould the safety device. This will also result in the needle-luer and safety device body becoming amalgamated.

Furthermore, instead of manufacturing the syringes separately from the safety device, the safety device could be manufactured at the same time as the syringe, possibly as a single integrated injection moulded device. In such a case, the device could be adapted to have either a conventional needle and needle-luer combination fitted to it or to have a needle mounted directly thereto with the device including a portion which performs the functions of a needle-luer as discussed above.

What is claimed is:

1. A safety device comprising:
   a needle fitting configured to mount with a needle;
   a sheath having a proximal end disposed with the needle fitting and a distal end, the sheath including elongated arms that extend between the proximal end and the distal end,
   a mid portion of the arms being pivotable towards and away from the needle to facilitate movement of the distal end of the sheath from a first position spaced from a distal end of the needle to a second position disposed adjacent a distal end of the needle;
   a resilient member engaging the arms to facilitate extension of the distal end of the sheath to the second position,
   wherein in the second position, the mid portion of the arms are in opposing relation with each other;
   wherein each of the elongated arms includes a front half and a back half, each back half being pivotally connected to its respective front half; and
   wherein the proximal end of the sheath is hingedly connected to a back member.

2. A safety device according to claim 1, wherein the back member is configured to attach to a needle receiving member.

3. A safety device according to claim 2, wherein the back member is configured to receive a needle-luer.

4. The safety device according to claim 1, wherein in the second position, the mid portion of each of the arms is positioned to be substantially abutting a needle.

5. The safety device according to claim 1, wherein when the sheath is in the second position, the sheath is configured such that a force applied to the distal end of the sheath urges the mid portion of each of the arms towards the other to maintain the sheath in the second position.

6. The safety device according to claim 5, wherein each of the arms is semi-elliptical and tapers radially inwardly towards the mid portion.

7. The safety device according to claim 1, wherein each of the arms is semi-elliptical and tapers radially inwardly towards the mid portion.

8. The safety device according to claim 1, wherein each of the arms includes an edge, the edges of each of the arms facing the edge of the other arm.

9. The safety device according to claim 8, wherein at least a portion of the edges of each of the arms abut in the second position.

10. The safety device according to claim 9, wherein the edge of each of the arms includes rounded interlocking teeth.

11. The safety device according to claim 8, wherein the edge of each of the arms has a depth of about 5 percent of the overall length of the device.

12. The safety device according to claim 8, wherein the edges are flat.

13. The safety device according to claim 1, wherein in the second position, the mid portion of each of the arms is positioned to be substantially abutting a needle and the proximal and distal ends of the arms are spaced radially outwardly of the mid portion.

14. A safety device comprising:
   a needle fitting configured to mount with a needle;
   a sheath having a proximal end disposed with the needle fitting and a distal end, the sheath including elongated arms that extend between the proximal end and the distal end,
   a mid portion of the arms being pivotable towards and away from the needle to facilitate movement of the distal end of the sheath from a first position spaced from a distal end of the needle to a second position disposed adjacent a distal end of the needle;
   a resilient member engaging the arms to facilitate extension of the distal end of the sheath to the second position,
   wherein in the second position, the mid portion of the arms are in opposing relation with each other; and
   further including a priming button positioned adjacent the proximal end of the sheath, the priming button being movable to move the elongated arms from their second position to their first position;
   wherein the priming button includes a first half formed on a first elongated arm of the elongated arms and a second half formed on a second elongated arm of the elongated arms.

* * * * *